United States Patent
Stubenrauch et al.

(10) Patent No.: US 10,168,326 B2
(45) Date of Patent: Jan. 1, 2019

(54) INTERFERENCE-SUPPRESSED IMMUNOASSAY TO DETECT ANTI-DRUG ANTIBODIES IN SERUM SAMPLES

(71) Applicant: Hoffmann-La Roche Inc., Littel Falls, NJ (US)

(72) Inventors: Kay-Gunnar Stubenrauch, Penzberg (DE); Rudolf Vogel, Weilheim (DE)

(73) Assignee: F. HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 15/078,140

(22) Filed: Mar. 23, 2016

(65) Prior Publication Data

US 2016/0313322 A1   Oct. 27, 2016

Related U.S. Application Data

(63) Continuation of application No. PCT/EP2014/063891, filed on Jul. 1, 2014.

(30) Foreign Application Priority Data

Jul. 4, 2013   (EP) .................................... 13175091

(51) Int. Cl.
| | |
|---|---|
| *G01N 33/53* | (2006.01) |
| *G01N 33/543* | (2006.01) |
| *C07K 16/28* | (2006.01) |
| *G01N 33/68* | (2006.01) |

(52) U.S. Cl.
CPC ... *G01N 33/54393* (2013.01); *C07K 16/2866* (2013.01); *G01N 33/6854* (2013.01); *C07K 2317/24* (2013.01)

(58) Field of Classification Search
CPC ..................... G01N 33/54393; G01N 33/6854
See application file for complete search history.

(56) References Cited

U.S. PATENT DOCUMENTS

| | | |
|---|---|---|
| 5,122,469 A | 6/1992 | Mather et al. |
| 5,480,796 A | 1/1996 | Kishimoto |
| 5,670,373 A | 9/1997 | Kishimoto |
| 5,795,965 A | 8/1998 | Tsuchiya et al. |
| 5,817,790 A | 10/1998 | Tsuchiya et al. |
| 5,821,121 A | 10/1998 | Brothers |
| 5,851,793 A | 12/1998 | Kishimoto |
| 5,888,510 A | 3/1999 | Kishimoto et al. |
| 5,990,282 A | 11/1999 | Kishimoto |
| 6,086,874 A | 7/2000 | Yoshida et al. |
| 6,156,570 A | 12/2000 | Hu et al. |
| 6,261,560 B1 | 7/2001 | Tsujinaka et al. |
| 6,284,453 B1 | 9/2001 | Siano |
| 6,406,909 B1 | 6/2002 | Shibuya et al. |
| 6,410,691 B1 | 6/2002 | Kishimoto |
| 6,428,979 B1 | 8/2002 | Kishimoto |
| 6,537,782 B1 | 3/2003 | Shibuya et al. |
| 6,692,742 B1 | 2/2004 | Nakamura et al. |
| 6,723,319 B1 | 4/2004 | Ito et al. |
| 6,875,432 B2 | 4/2005 | Liu et al. |
| 6,962,812 B2 | 11/2005 | Shibuya et al. |
| 7,320,792 B2 | 1/2008 | Ito et al. |
| 7,332,289 B2 | 2/2008 | Takeda et al. |
| 7,479,543 B2 | 1/2009 | Tsuchiya et al. |
| 7,498,031 B2 | 3/2009 | Fujioka et al. |
| 7,521,052 B2 | 4/2009 | Okuda et al. |
| 7,566,453 B2 | 7/2009 | Nakamura et al. |
| 7,666,413 B2 | 2/2010 | Liu et al. |
| 7,771,723 B2 | 8/2010 | Nakamura et al. |
| 7,824,674 B2 | 11/2010 | Ito et al. |
| 7,927,815 B2 | 4/2011 | Takeda et al. |
| 7,955,598 B2 | 6/2011 | Yoshizaki et al. |
| 8,017,121 B2 | 9/2011 | Kishimoto et al. |
| 8,142,776 B2 | 3/2012 | Liu et al. |
| 8,173,126 B2 | 5/2012 | Yoshizaki et al. |
| 8,227,195 B2 * | 7/2012 | Stubenrauch .......... G01N 33/94 435/7.1 |
| 8,398,980 B2 | 3/2013 | Kano et al. |
| 8,420,789 B2 | 4/2013 | Takeda et al. |
| 8,440,196 B1 | 5/2013 | Funakoshi et al. |

(Continued)

FOREIGN PATENT DOCUMENTS

| | | |
|---|---|---|
| EP | 409607 | 1/1991 |
| EP | 05 677 38 A2 | 11/1993 |

(Continued)

OTHER PUBLICATIONS

"European Search Report in EP09013455".
"International Search Report in PCT/EP2010/066073".
"ProCHO TM Protein-free CHO medium [online catalog entry]", Available on line at <https://bcprd.lonza.com/shop/b2c/display/(xcm-lonza b2b&layout=5.16_1_75_65_811&uiarea=2&carea-DCEA2D5E710D138F18C7C001A4B525E107cpgnum=1)/.d0 >, accessed Nov. 30, 2009.
Åkesson, et. al., "Probing control of fed-batch cultivations: analysis and tuning", Control Engineering Practice, 2001, vol. 9, pp. 709-723.
Altamirano et al., "Decoupling Cell Growth and Product Formation in Chinese Hamster Ovary Cells Through Metabolic Control" Biotechnology and Bioengineering 76:351-360 (2001).
Alton et al., "Direct utilization of mannose for mammalian glycoprotein biosynthesis" Glycobiology 8(3):285-295 ( 1998).

(Continued)

*Primary Examiner* — Prema M Mertz
(74) *Attorney, Agent, or Firm* — Foley & Lardner LLP

(57) ABSTRACT

Herein is reported an enzyme linked immunosorbent assay for the detection of anti-drug antibodies against a drug antibody in a sample comprising a capture drug antibody and a tracer drug antibody, wherein the capture drug antibody and the tracer drug antibody are employed in a concentration of 0.5 µg/ml or more, the sample is incubated simultaneously with the capture drug antibody and the tracer drug antibody for 1 to 24 hours, the capture drug antibody and the tracer drug antibody are derivatized via a single lysine residue, the sample comprises 10% serum, and oligomeric human IgG is added to the sample prior to the incubation with the capture drug antibody and the tracer drug antibody.

7 Claims, 8 Drawing Sheets

(56) References Cited

U.S. PATENT DOCUMENTS

| | | |
|---|---|---|
| 8,470,316 B2 | 6/2013 | Yasunami |
| 2001/0001663 A1 | 5/2001 | Kishimoto et al. |
| 2002/0045571 A1 | 4/2002 | Liu et al. |
| 2002/0131967 A1 | 9/2002 | Nakamura et al. |
| 2002/0187150 A1 | 12/2002 | Mihara et al. |
| 2003/0170813 A1 | 9/2003 | Suga et al. |
| 2003/0190316 A1 | 10/2003 | Kakuta et al. |
| 2004/0071706 A1 | 4/2004 | Ito et al. |
| 2004/0115197 A1 | 6/2004 | Yoshizaki et al. |
| 2004/0247621 A1 | 12/2004 | Nahamura et al. |
| 2005/0070013 A1 | 3/2005 | Luan et al. |
| 2005/0118163 A1 | 6/2005 | Mizushima et al. |
| 2005/0142635 A1 | 6/2005 | Tsuchiya et al. |
| 2005/0175603 A1 | 8/2005 | Liu et al. |
| 2005/0214278 A1 | 9/2005 | Kakuta et al. |
| 2005/0238644 A1 | 10/2005 | Mihara et al. |
| 2006/0127975 A1 | 6/2006 | Link et al. |
| 2006/0134113 A1 | 6/2006 | Mihara |
| 2006/0142549 A1 | 6/2006 | Takeda et al. |
| 2006/0165696 A1 | 7/2006 | Okano et al. |
| 2006/0292147 A1 | 12/2006 | Yoshizaki et al. |
| 2007/0036785 A1 | 2/2007 | Kishimoto et al. |
| 2007/0098714 A1 | 5/2007 | Nishimoto et al. |
| 2007/0116700 A1 | 5/2007 | Liu et al. |
| 2007/0134242 A1 | 6/2007 | Nishimoto et al. |
| 2007/0141675 A1 | 6/2007 | Suga et al. |
| 2007/0148169 A1 | 6/2007 | Yoshizaki et al. |
| 2007/0243189 A1 | 10/2007 | Yoshizaki et al. |
| 2008/0124325 A1 | 5/2008 | Ito et al. |
| 2008/0124761 A1 | 5/2008 | Goto et al. |
| 2008/0255342 A1 | 10/2008 | Takeda et al. |
| 2008/0274106 A1 | 11/2008 | Nishimoto et al. |
| 2008/0306247 A1 | 12/2008 | Mizushima et al. |
| 2009/0022716 A1 | 1/2009 | Rockwell et al. |
| 2009/0061466 A1 | 3/2009 | Hoesel et al. |
| 2009/0131639 A1 | 5/2009 | Kakuta et al. |
| 2009/0181029 A1 | 7/2009 | Okuda et al. |
| 2009/0220499 A1 | 9/2009 | Yasunami |
| 2009/0220500 A1 | 9/2009 | Kobara |
| 2009/0263384 A1 | 10/2009 | Okada et al. |
| 2009/0269335 A1 | 10/2009 | Nakashima et al. |
| 2009/0291076 A1 | 11/2009 | Morichika et al. |
| 2009/0311718 A1 | 12/2009 | Fukushima et al. |
| 2010/0008907 A1 | 1/2010 | Nishimoto et al. |
| 2010/0034811 A1 | 1/2010 | Ishida |
| 2010/0061986 A1 | 3/2010 | Takahashi et al. |
| 2010/0129355 A1 | 5/2010 | Ohguro et al. |
| 2010/0129357 A1 | 5/2010 | Garcia-Martinez et al. |
| 2010/0247523 A1 | 9/2010 | Kano et al. |
| 2010/0255007 A1 | 10/2010 | Mihara et al. |
| 2010/0285011 A1 | 11/2010 | Morichika et al. |
| 2010/0291627 A1 | 11/2010 | Yamada et al. |
| 2010/0304400 A1 | 12/2010 | Stubenrauch et al. |
| 2011/0053223 A1 | 3/2011 | Bayer et al. |
| 2011/0150869 A1 | 6/2011 | Mitsunaga et al. |
| 2011/0206664 A1 | 8/2011 | Yoshizaki et al. |
| 2011/0245473 A1 | 10/2011 | Igawa et al. |
| 2011/0262462 A1 | 10/2011 | Platt et al. |
| 2011/0268734 A1 | 11/2011 | Ito et al. |
| 2012/0009177 A1 | 1/2012 | Platt et al. |
| 2012/0064086 A1 | 3/2012 | Liu et al. |
| 2012/0076783 A1 | 3/2012 | Liu et al. |
| 2012/0183539 A1 | 7/2012 | Maeda |
| 2012/0219974 A1 | 8/2012 | Stubenrauch et al. |
| 2012/0301460 A1 | 11/2012 | Bao et al. |

FOREIGN PATENT DOCUMENTS

| | | |
|---|---|---|
| EP | B1 0 387 840 | 7/1994 |
| EP | 628639 | 12/1994 |
| EP | 1 585 810 B1 | 3/2010 |
| EP | B1 1 585 810 | 3/2010 |
| JP | 01-101882 | 4/1989 |
| JP | 7258252 | 10/1995 |
| JP | 08099902 | 4/1996 |
| JP | 03630453 B2 | 3/2006 |
| JP | 03822137 B2 | 9/2006 |
| WO | WO 1992/19759 | 11/1992 |
| WO | WO 1993/022448 | 11/1993 |
| WO | WO 1996/039488 | 12/1996 |
| WO | WO 1997/026334 | 7/1997 |
| WO | WO 1998/041611 | 9/1998 |
| WO | WO 2000/010607 A1 | 3/2000 |
| WO | WO 2002/002793 | 1/2002 |
| WO | WO 2002/013859 A1 | 2/2002 |
| WO | WO 2002/033109 A2 | 4/2002 |
| WO | WO 2002/076578 A1 | 10/2002 |
| WO | WO 2002/101019 A2 | 12/2002 |
| WO | WO 2004/041216 A2 | 5/2004 |
| WO | WO 2004/048556 | 6/2004 |
| WO | WO 2004/104186 A1 | 12/2004 |
| WO | WO 2005/061000 | 7/2005 |
| WO | WO 2008/016134 A1 | 2/2008 |
| WO | WO 2008/078715 A1 | 7/2008 |
| WO | WO 2009/014263 | 1/2009 |
| WO | WO 2009/044774 | 4/2009 |
| WO | WO 2009/092508 A | 4/2009 |
| WO | WO 2009/077127 A1 | 6/2009 |
| WO | WO 2009/084659 | 9/2009 |
| WO | WO 2009/112250 | 9/2009 |
| WO | WO 2009/114641 A1 | 9/2009 |
| WO | WO 2011/051231 A1 | 5/2011 |
| WO | WO 2011/149046 A1 | 12/2011 |
| WO | WO 2011/149051 A1 | 12/2011 |
| WO | WO 2012/064627 A2 | 5/2012 |
| WO | WO 2013/031237 A1 | 3/2013 |

OTHER PUBLICATIONS

Araujo, et al., "Increased rheumatoid factor interference observed during immunogenicity assessment of an Fc-engineered therapeutic antibody," J. Pharm. Biomed. Analysis 2011, vol. 55, pp. 1041-1049.

Ashwell and Harford, "Carbohydrate-specific receptors of the liver" Annu Rev Biochem 51:531-554 ( 1982).

Baenziger, J., "The role of glycosylation in protein recognition" Am J Pathol 121:382-391 ( 1985).

Baker et al., "Metabolic Control of Recombinant Protein N-Glycan Processing in NS0 and CHO Cells" Biotechnology and Bioengineering 73:188-202 (2001).

Barford, et. al., "Enhancement of Productivity by Yield Improvements Using Simulation Techniques", Animal Cell Technology: Basic and Applied Aspects, H. Murakami, et. al., Kluwer Academic Publishers, 1992, pp. 397-403.

Baumann et al., "Glucose Starvation Leads in Rat Hepatoma Cells to Partially N-Glycosylated Glycoproteins Including α 1-Acid Glycoproteins" The Journal of Biological Chemistry 258:3942-3949 (1983).

Bernard, A.R. Production of Proteins by Transient Expression, Serono Pharmaceutical Research Institute, Chapter 17, pp. 605-626.

Bilbia, et. al., "In Pursuit of the Optimal Fed-Batch Process for Monoclonal Antibody Production", Biotechnol. Prog., 1995, vol. 11, pp. 1-13.

Borys et al., "Culture pH Affects Expression Rates and Glycosylation of Recombinant Mouse Placental Lactogen Proteins by Chinese Hamster Ovary (CHO) Cells" Bio/Technology 11:720-724 (Jun 1993).

Bourdage et al., "Effect of double antigen bridging immunoassay format on antigen coating concentration dependence and implications for designing immunogenicity assays for monoclonal antibodies," J. Pharmaceut. Biomed. Anal. 2005, vol. 39, pp. 685-690.

Bradshaw et al., "The hormonal control of protein N-glycosylation in the developing rabbit mammary gland and its effect upon transferrin synthesis and secretion" Biochim Biophys Acta 847:344-351 ( 1985).

Butler, M. "Animal cell cultures: recent achievements and perspectives in the production of biopharmaceuticals", Applied Microbiology and Biotechnology 68(3):283-291, 2005.

Chan and Wolf, "The role of vitamin A in the glycosylation reactions of glycoprotein synthesis in an 'in vitro' system" Biochem J 247:53-62 ( 1987).

(56) References Cited

OTHER PUBLICATIONS

Chapman et al., "Effects of glucose starvation and puromycin treatment on lipid-linked oligosaccharide precursors and biosynthetic enzymes in Chinese hamster ovary cells in vivo and in vitro" Archives of Biochemistry and Biophysics 260(1):320-333 (Jan. 1988).
Communication of the Examination Division dated May 8, 2007 relating to EP 04 752 591.0 (5 pages).
Crowley, J., "Effect of dilution rate on the metabolism and product formation" Animal Cell Culture and Production of Biologicals, Kensington, AU:University of NSW pp. 275-281 (1991).
Cruz, et. al., "Metabolic Shifts by Nutrient Manipulation in Continuous Cultures of BHK Cells", Biotechnol. and Bioengineering, 1999, vol. 66, pp. 104-113.
Cruz, et. al., "Metabolic Shifts Do Not Influence the Glycosylation Patterns of a Recombinant Fusion Protein Expressed in BHK Cells", Biotechnol. and Bioengineering, 2000, vol. 69, pp. 129-139.
Cruz, et. al., "Metabolically optimised BHK cell fed-batch cultures", J. Biotechnol., Jun. 2000, vol. 60, No. 2, pp. 109-118.
Dalili et al., "Glutamine-Limited Batch Hybridoma Growth and Antibody Production: Experiment and Model" Biotechnology and Bioengineering 36(36):74-82 (1990).
Davidson et al., "Sindbis Virus Glycoproteins are Abnormally Glycosylated in Chinese Hamster Ovary Cells Deprived of Glucose" J. Gen. Virol. 66:1457-1468 (1985).
De Buyl, et. al., "Fed-batch culture development based on biomass monitoring", New Developments and New Applications in Animal Cell Technology, O.W. Merlen, et. al., Kluwer Academic Publishers, 1998, pp. 337-342.
De Tremblay, et. al., "Fed-batch culture of hybridoma cells: comparison of optimal control approach and closed loop strategies", Bioprocess Engineering, 1993, vol. 9, pp. 13-21.
De Tremblay, et. al., "Optimization of fed-batch culture of hybridoma cells using dynamic programming: single and multi feed cases", Bioprocess Engineering, 1992, vol. 7, pp. 229-234.
Declaration of Dr. Christoph Holzke dated Dec. 3, 2012 (1 page).
Declaration of Dr. Denis Drapeau in Opposition of European Patent No. EP1623019B1 dated Dec. 3, 2012 (7 pages).
Domach, et. al., Computer Model for Glucose-Limited Growth of a Single Cell of *Escherichia coli* Br/A, Biotechnol. and Bioeng., 1984, vol. XXVI, 203-216.
Dowd et al., "Glucose-Based Optimization of CHO-Cell Perfusion Cultures" Biotechnology and Bioengineering 75:252-256 (2001).
Dowd et al., "Predictive Control of Hollow-Fiber Bioreactors for the Production of Monoclonal Antibodies" Biotechnology and Bioengineering 63:484-492 (1999).
Dwek et al., "Glycobiology: 'The function of sugar in the IgG molecule'" J Anat 187:279-292 (Oct. 1995).
Eagle, Harry, "Amino Acid Metabolism in Mammalian Cell Cultures", Science, Aug. 1959, vol. 130, No. 3373, pp. 432-437.
Elbein, A., "Inhibitors of the Biosynthesis and Processing of N-Linked Oligosaccharides" CRC Critical Reviews 16(1):21-49 (1984).
Elbein, A., "Inhibitors of the Biosynthesis and Processing of N-Linked Oligosaccharide Chains" Annual Review of Biochemistry 56:497-534 (1987).
Endo et al., "Glycosylation of the variable region of immunoglobulin G—site specific maturation of the sugar chains" Mol Immunol 32(13):931-940 ( 1995).
EP Search Report in EP 10176622 dated Apr. 19, 2012.
EP Search Report in EP10152393 dated Jul. 27, 2010.
Essers et al., "Bioprocess development for the production of a prospective tumor vaccine expressed by CHO cells in protein-free medium" Poster LifeTec Xchange Congress 'Technologies for Life Sciences', Aachen, Germany, pp. 1 (2003).
Europa, et. al., "Multiple Steady States with Distinct Cellular Metabolism in Continuous Culture of Mammalian Cells", Biotechnology and Bioengineering, 2000, vol. 67, pp. 25-34.
Excerpt from Biochrom Product Information Catalogue, "Ham's F-12 liquid medium", 2015, p. 47.

Exhibit A in Declaration of Dr. Christoph Holzke, internal database caltoguing and warehousing system confirming receipt of Thesis by Thomas Link dated Mar. 11, 2004 (1 page).
Feizi and Childs, "Carbohydrates as antigenic determinants of glycoproteins" Biochem J 245:1-11 ( 1987).
Fleischaker, R.J., "An Experimental Study in the Use of Instrumentation to Analyze Metabolism and Product Formation in Cell Culture" Ph.D. Thesis Submitted to Massachusetts Institute of Technology (Jun. 1982).
Frahm, et. al., "Adaptive Model-Based Control by the Open-Loop-Feedback-Optimal (OLFO) Controller for the Effective Fed-Batch Cultivation of Hyridoma Cells", Biotechnol. Prog., 2002, vol. 18, pp. 1095-1103.
Frame, et. al., "Oxygen Uptake of Mammalian Cells in Microcarrier Culture—Response to Changes in Glucose Concentration", Biotechnology Letters, 1985,vol. 7, No. 3, pp. 147-152.
Fu, et. al., "Metabolic Flux Distributions in Hybridoma Cells at Different Metabolic Rates", Animal Cell Technology Developments Towards the 21st Century, 1999, pp. 51-55.
Gambhir, et. al., "Alteration of Cellular Metabolism by Consecutive Fed-Batch Cultures of Mammalian Cells", Journal of Bioscience and Bioengineering, vol. 87, No. 6, pp. 805-810.
Gawlitzek et al., "Characterization of changes in the glycosylation pattern of recombinant proteins from BHK-21 cells due to different culture conditions" Journal of Biotechnology 42:117-131 (1995).
Gawlitzek et al., "Effect of Different Cell Culture Conditions on the Polypeptide Integrity and N-Glycosylation of a Recombinant Model Glycoprotein" Biotechnology and Bioengineering 46:536-544 (1995).
Genentech, Inc., "ACTEMRA (tocilizumab) Injection, for intravenous infusion" (U.S. Prescribing Information) pp. 1-24 (2010).
Geng et al., "Validation of immunoassays used to assess immunogenicity to therapeutic monoclonal antibodies," J. Pharm. Biomed. Anal. 2005, vol. 39, pp. 364-375.
Genovese et al., "Interleukin-6 receptor inhibition with tocilizumab reduces disease activity in rheumatoid arthritis with inadequate response to disease-modifying antirheumatic drugs: The tocilizumab in combination with traditional disease-modifying antirheumatic drug therapy study" Arthritis & Rheumatism 58(10):2968-2980 (Oct. 2008).
Gershman et al., "Transitory Effects of Glucose Starvation on the Synthesis of Dolichol-linked Oligosaccharides in Mammalian Cells" The Journal of Biological Chemistry 256(15):7774-7780 (1981).
Glacken, et. al., "Mathematical descriptions of hybridoma culture kinetics. III. Simulation of fed-batch bioreactors", Journal of Biotechnology, 1989, vol. 10, pp. 39-66.
Glacken, et. al., "Reduction of Waste Product Excretion via Nutrient Control: Possible Strategies for Maximizing Product and Cell Yields on Serum in Cultures of Mammalian Cells", Biotechnol. and Bioengineering, 1986, vol. XXVIII, pp. 1376-1389.
Glacken, M.W., "Development of Mathematical Descriptions of Mammalian Cell Culture Kinetics for the Optimization of Fed-Batch Bioreactors" Ph.D. Thesis submitted to Massachusetts Institute of Technology for the Degree of Doctor of Science in Biochemical Engineering (Apr. 1987).
Goetze et al., "High-mannose glycans on the Fc region of therapeutic IgG antibodies increase serum clearance in humans" Glycobiology 21(7):949-959 (Jul. 2011).
Griffiths, B., "Perfusion Systems for Cell Cultivation" Large-Scale Mammalian Cell Culture Technology, Lubiniecki, A.S., New York and Basel:Marcel Dekker, Inc., Chapter 9, pp. 217-250 (1990).
Guan et al., "On-line heatflux measurements improve the culture medium for the growth and productivity of genetically engineered CHO cells" Cytotechnology 30:107-120 (1999).
Guardia et al., "Cybernetic Modeling and Regulation of Metabolic Pathways in Multiple Steady States of Hybridoma Cells" Biotechnology Progress 16:847-853 (2000).
Häggström, et. al., "Metabolic Engineering of Animal Cells", Annals of the New York Academy of Sciences, 1996, vol. 782, pp. 40-52.
Hahn et al., "Growth-associated Glycosylation of Transferrin Secreted by HepG2 Cells" The Journal of Biological Chemistry 267:23982-23987 (1992).

(56) References Cited

OTHER PUBLICATIONS

Ham, et. al., "Media and Growth Requirements", Methods in Enzymology, vol. LVIII, Jakoby and Pastan, Academic Press, New York, 1979, pp. 44-93.

Ham, Richard G., "Clonal Growth of Mammalian Cells in a Chemically Defined Synthetic Medium", Proc. Nat. Acad. Sci. U.S.A., Feb. 1965, vol. 53, No. 2, pp. 288-293.

Hayter et al., "Chinese Hamster Ovary Cell Growth and Interferon Production Kinetics in Stirred Batch Culture" Applied Microbiology and Biotechnology 34:559-564 (1991).

Hayter, et. al., "Glucose-Limited Chemostat Culture of Chinese Hamster Ovary Cells Producing Recombinant Human Interferon-γ", Biotechnol. and Bioengineering, 1992, vol. 39, pp. 327-335.

Higareda, et. al., "The Use of culture Redox Potential and Oxygen Uptake Rate for Assessing Glucose and Glutamine Depletion in Hybridoma Cultures", Biotechnol. and Bioengineering, 1997, vol. 56, pp. 555-563.

Hills et al., "Metabolic control of recombinant monoclonal antibody N-glycosylation in GS-NS0 cells" Biotechnol Bioeng 75:239-251 ( 2001).

Hu, et. al., "Controlling Mammalian Cell Metabolism in Bioreactors", J. Microbiol. Biotechnol., 1998, vol. 8, No. 1, pp. 8-13.

Hu, et. al., "Effect of glucose on the cultivation of mammalian cells", Developm. Biol. Standard, 1987, vol. 66, pp. 279-290.

Hu, et. al., "Toward Advanced Nutrient Feeding in Animal Cell Culture", Harnessing Biotechnology for the 21st Century, 1992, pp. 202-205.

Ip et al., "Structural characterization of the N-glycans of a humanized anti-CD18 murine immunoglobulin G" Arch Biochem Biophys 308(2):387-399 (Feb. 1994).

Jayme, et. al., "Basal medium development for serum-free culture: a historical perspective", Cytotechnology, Jan. 1997, vol. 1, No. 3, pp. 95-101.

Jefferis et al., "Glycosylation of antibody molecules: structural and functional significance" Chem. Immunol. 65:111-128 (1997).

Jefferis, Royston, "Glycosylation of recombinant antibody therapeutics" Biotechnol Prog 21(1):11-16 (Jan. 2005).

Jenkins et al., "Getting the glycosylation right: Implications for the biotechnology industry" Nature Biotechnology 14:975-981 (1996).

Kaliyaperumal et al., "Immunogenicity assessment of therapeutic proteins and peptides," Curr. Pharm. Biotechnol. 2010, vol. 10, pp. 352-358.

Kanda et al., "Comparison of biological activity among nonfucosylated therapeutic IgG1 antibodies with three different N-linked Fc oligosaccharides: the high-mannose, hybrid, and complex types" Glycobiology 17(1):104-118 ( 2006).

Kitos et al., "Glucose Metabolism by Mouse Cells (NCTC Clone 929) Under Conditions of Defined Nutrition" Experimental Cell Research 35:108-118 (1964).

Kleman, et. al., "A Predictive and Feedback Control Algorithm Maintains a Constant Glucose Concentration in Fed-Batch Fermentations", Applied and Environmental Microbilogy, Apr. 1991, vol. 57, No. 4, pp. 910-917.

Kompala et al., "Optimization of High Cell Density Perfusion Bioreactors" Cell Culture Technology for Pharmaceutical and Cell-Based Therapies, Ozturk, S.S. and Hu, W.S. (eds.), Chapter 11, pp. 387-416 (2006).

Kondo et al., "Improved Method for Fluorescence Labeling of Sugar Chains with Sialic Acid Residues" Agricultural and Biological Chemistry 54:2169-2170 (1990).

Konstantinov, et. al., "Advantages and Disadvantages of Glucose Limitation in Perfused Mammalian Cell Cultures", Animal Cell Technology: Developments towards the 21st Century, E. C. Beavery, et. al., Kluwer Academic Publishers, 1995, pp. 567-573.

Krapp et al., "Structural analysis of human IgG-Fc glycoforms reveals a correlation between glycosylation and structural integrity" J Mol Biol 325(5):979-989 (Jan. 31, 2003).

Kunkel et al., "Dissolved oxygen concentration in serum-free continuous culture affects N-linked glycosylation of a monoclonal antibody" J Biotechnol 62:55-71 ( 1998).

Kurokawa et al., "Growth Characteristics in Fed-Batch Culture of Hybridoma Cells with Control of Glucose and Glutamine Concentrations" Biotechnology and Bioengineering 44:95-103 (1994).

Kurokawa, et. al., "Kinetic Study of Hybridoma Metabolism and Antibody Production in Continuous Culture Using Serum-Free Medium", Journal of Fermentation and Bioengineering, 1993, vol. 76, pp. 128-133.

Lee, et. al., "Control of fed-batch fermentations", Biotechnology Advances, 1999, vol. 17, pp. 29-48.

Lenas, et. al., "Adaptive Fuzzy Control of Mammalian Cell Culture in Fed-Batch Reactor for Production of an Antithrombin III Variant", Animal Cell Technology: Basic and Applied Aspects, 1998, vol. 9, pp. 217-221.

Levering, et. al., "Physiology of myeloma cells grown in glucose-limited chemostat cultures", Cytotechnology, 1992, vol. 9, pp. 125-130.

Lin et al., "Production of tPA in Recombinant CHO Cells Under Oxygen-Limited Conditions" Biotechnology and Bioengineering 42:339-350 (1993).

Lin, et. al., "Determination of the Maximum Specific Uptake Capacities for Glucose and Oxygen in Glucose-Limited Fed-Batch Cultivations of *Eschericha coli*", Biotechnology and Bioengineering, 2001, vol. 73, pp. 347-357.

Link et al., "Process Development for the Large Scale Production of human Mucins with recombinant CHO Cells" Slides 7th Int. Workshop on Carcinoma-associate mucins, Crete, Greece, pp. 1-4 ( Apr. 3, 2003).

Link Ph.D. thesis, Date: Feb. 2004 (in German with English Abstract) (175 pages).

Link, et. al., "Development of a metabolically optimized fermentation process based on glucose-limited CHO perfusion culture", Animal Cell Technology Meets Genomics, F. Gòdia and M. Fussenegger, Springer, 2005, pp. 423-430.

Linz, et. al., "Stoichiometry, Kinetics, and Regulation of Glucose and Amino Acid Metabolism of a Recombinant BHK Cell Line in Batch and Continuous Cultures", Biotechnol. Prog., 1997, vol. 13, pp. 453-463.

Ljunggren et al., "Specific growth rate as a parameter for tracing growth-limiting substances in animal cell cultures" Journal of Biotechnology 42:163-175 (1995).

Ljunggren, et. al., "Catabolic control of hybridoma cells by glucose and glutamine limited fed batch cultures", Biotechnol. Bioeng., Sep. 1994, vol. 44, No. 7, pp. 808-818.

Lonza, ProCHO///superscript:TM/// Protein-free CHO Medium, pp. 1 (Retrieved on internet Nov. 30, 2009).

Lübben, Holger, "Diauxic Cell Behavior Enables Detoxification of CHO Cell Culture Medium During Fed Batch Cultivation", New Developments and New Applications in Animal Cell Technology, O.W. Marten, Kluwer Academic Publishers, 1998, pp. 267-271.

Lübben, Holger, Dissertation of the University of Hannover, Germany, 1997, pp. 1-157 (in German with English Abstract).

Lüdemann, et. al., "Effects of NH3 on the cell growth of a hybridoma cell line", Cytotechnology, 1994, vol. 14, pp. 11-20.

Lüdemann, Fortschrittsberichte, VDI 17, Nr. 164, 1997, pp. 1-152 (Excerpt in English).

Luli, et. al., "Comparison of Growth, Acetate Production and Acetate Inhibition of *Eschericha coli* Strains in Batch and Fed-Batch Fermentations", Applied and Environmental Microbiology, Apr. 1990. vol. 56, No. 4, pp. 1004-1011.

Lund et al., "Control of IgG/Fc Glycosylation: A Comparison of Oligosaccharides from Chimeric Human/Mouse and Mouse Subclass Immunoglobulin Gs" Mol Immunol 30(8):741-748 ( 1993).

Lund et al., "Multiple Interactions of the IgG with Its Core Oligosaccharide can Modulate Recognition by Complement and Human Fcγ Receptor I and Influence the Synthesis of Its Oligosaccharide Chains" J Immunol 157:4963-4969 ( 1996).

Lund et al., "Oligosaccharide-protein interactions in IgG can modulate recognition by Fcγ receptors" FASEB J 9:115-119 ( 1995).

Lydersen, B.K., "Perfusion Cell Culture System Based on Ceramic Matrices" Large Scale Animal Culture, Munich:Hanser Publishers pp. 169-192 (1987).

(56) References Cited

OTHER PUBLICATIONS

Marique, et. al., A general artificial neural network for the modelization of culture kinetics of different CHO strains, Cytotechnology, 2001, vol. 36, pp. 55-60.
Mather et al., "Culture Media, Animal Cells, Large Scale Production" Encyclopedia of Bioprocess Technology: Fermentation, Biocatalysis, and Bioseparation, Flickinger, M.C. and Drew, S.W., John Wiley & Sons, Inc. vol. 2:777-785 (1999).
McFarlane, I.G., "Hepatic clearance of serum glycoproteins" Clin Sci 64:127-135 ( 1983).
Meijer et al., "Effects of Glucose Supply on Myeloma Growth and Metabolism in Chemostat Culture" Journal of Cellular Physiology 162:191-198 (1995).
Michel-Savia, et. al., "Control of the selectivity of butyric acid production and improvement of fermentation performance with *Clostridium tyrobutyricum*", Appl. Microbiol. Biotechnol., 1990, vol. 32, pp. 387-392.
Mikulskis et al., "Solution ELISA as a platform of choice for development of robust, drug tolerant immunogenicity assays in support of drug development," J. Immunol. Methods 2011, vol. 365 pp. 38-49.
Millward et al., "Effect of constant and variable domain glycosylation on pharmacokinetics of therapeutic antibodies in mice" Biologicals 36:41-47 ( 2008).
Mimura et al. et al., "The influence of glycosylation on the thermal stability and effector function expression of human IgG1-Fc: properties of a series of truncated glycoforms" Mol Immunol 37(12-13):697-706 (Aug. 2000).
Mimura et al., "Role of Oligosaccharide Residues of IgG1-Fc in FcγRIIb Binding" J Biol Chem 276(49):45539-45547 (Dec. 7, 2001).
Mire-Sluis et al., "Recommendations for the design and optimization of immunoassays used in the detection of host antibodies against biotechnology products," J. Immunol. Methods 2004, vol. 289, pp. 1-16.
Mizrahi, Avshelom, "Techniques and Equipment for Animal Cell Cultivation", European Society for Animal Cell Technology, 9th Meeting, 1988, pp. 314-321.
Mizuochi et al., "Structures of the sugar chains of mouse immunoglobulin G 1" Arch Biochem Biophys 257(2):387-394 ( 1987).
Muthing et al., "Effects of Buffering Conditions and Culture pH on Production Rates and Glycosylation of Clinical Phase I Antimelanoma Mouse IgG3 Monoclonal Antibody R24" Biotechnology and Bioengineering 83:321-334 (2003).
Nielsen et al., "Avoiding rapid growth at high cell densities: A potentially important optimisation criterion for hybridoma cultures" Cytotechnology 9:21-27 (1992).
Niloperbowo, et. al., "Improved Monoclonal Antibody Production via Controlled Feeding Strategies During Fedbatch Cultures of Hybridoma Cell Line Utilizing Protein Free Media", Animal Cell Technology: Basic and Applied Aspects, S. Kaminogawa, et. al., Kluwer Academic Publishers, 1993, pp. 409-415.
Noll, et. al., "Development of a metabolically optimized fermentation process based on a glucose-limited CHO perfusion culture", 18th Annual ESACT Meeting, May 11-15, 2003, Granada, Spain, abstract O-5.06, p. 75.
Noll, T., "Glucose limitation in mammalian cell culture: starvation to success?—Development of a metabolically optimized fermentation process based on CHO perfusion culture" Slides JAACT, Nagoya, Japan, pp. 1-32 ( Nov. 16, 2004).
Noll, T., "Glucose-limited mammalian cell culture for the production of recombinant proteins" Slides Workshop on 'Production of biopharmaceuticals in animal cell cultures', Rio de Janeiro, Brazil, pp. 1-50 ( Jul. 13, 2004).
Noll, T., "Produktion rekombinanter Proteine mit Säugerzellen—Beiträge zur Prozessentwicklung" Slides Probiogen AG, Berlin, Germany, pp. 1-31 ( Jun. 24, 2003).
Noll, T., "Produktion rekombinanter Proteine mit Säugerzellen—Beiträge zur Prozessentwicklung" Slides Penzberg, Germany, pp. 1-37 ( Jan. 31, 2003).
Noll, T., "Vervielfachung der Produktivität von CHO Zellen durch eine neue Prozessstrategie" Slides GVC/Dechema Vortrags—und Diskussionstagung 'Zellkulturen: Vom biologischen System zum Produktionsprozess', Bad Dürkheim, Germany, pp. 1-32 ( May 26, 2003).
Noll, Thomas, "Development of a metabolically optimized fermentation process based on glucose-limited CHO perfusion culture", Slides presented at the 18th Annual ESACT Meeting, May 2003, Granada, Spain (24 pages).
Oh, et. al., "Interactive Dual Control of Glucose and Glutamine Feeding in Hybridoma Cultivation", Journal of Fermentation and Bioengineering, 1996, vol. 81, No. 4, pp. 329-336.
Omasa, et. al., "Effects of Lactate Concentration on Hybridoma Culture in Lactate-Controlled Fed-Batch Operation", Biotechnology and Bioengineering, 1992, vol. 39, pp. 556-564.
Paalme, et. al., "Glucose-Limited Fed-Batch Cultivation of *Escherichia coli* with Computer-Controlled Fixed Growth Rate", Biotechnology and Bioengineering, 1990, vol. 35, pp. 312-319.
Pan et al., "Comparison of the NIDS® rapid assay with ELISA methods in immunogenicity testing of two biotherapeutics," J. Pharmacolog. Toxicolog. Methods 2011, vol. 63, No. 2, pp. 150-159.
Parekh et al., "Association of rheumatoid arthritis and primary osteoarthritis with changes in the glycosylation pattern of total serum IgG" Nature 316:452-457 ( 1985).
Patel et al., "Different culture methods lead to differences in glycosylation of a murine IgG monoclonal antibody" Biochemistry J 285:839-845 ( 1992).
Peipp et al., "Molecular Engineering III: Fc Engineering" Handbook of Therapeutic Antibodies, Stefan Dubel, Wiley-VCH pp. 171-196 (2007).
Pendley et al., "Bioanalytical interferences in immunoassays for antibody biotherapeutics," Bioanalysis 2011, vol. 3, No. 7, pp. 703-706.
Petrova, et. al., "Neural network modelling of fermentation processes. Microorganisms cultivation model", Bioprocess Engineering, 1997, vol. 16, pp. 145-159.
Petrova, et. al., "Neural network modelling of fermentation processes. Specific growth rate model", Bioprocess Engineering, 1998, vol. 18, pp. 281-287.
Pfaff, et. al., "Model-Aided On-Line Glucose Monitoring for Computer-Controlled High Cell Density Fermentation", Computer applications in biotechnology: a post print volume from the 6th International Conference, Garmisch-Paretenkirchen, Germany, A. Munack and K. Schügerl, Pergamon, 1995, pp. 6-11.
Pörtner, et. al., "High density fed-batch cultures for hybridoma cells performed with the aid of a kinetic model", Bioprocess Engineering, 1996, vol. 15, pp. 117-124.
Qiu et al. "A novel homogeneous Biotin-digoxigenin based assay for the detection of human anti-therapeutic antibodies in autoimmune serum," J. Immunol. Methods 2010, vol. 362, pp. 101-111.
Rearick et al., "Glucose Starvation Alters Lipid-linked Oligosaccharide Biosynthesis in Chinese Hamster Ovary Cells" The Journal of Biological Chemistry 256:6255-6261 (1981).
Rifai et al., "The N-Glycans Determine the Differential Blood Clearance and Hepatic Uptake of Human Immunoglobulin (Ig)A1 and IgA2 Isotypes" J Exp Med 191:2171-2181 ( 2000).
Robinson et al., "Characterization of a Recombinant Antibody Produced in the Course of a High Yield Fed-Batch Process" Biotechnol Bioeng 44:727-735 ( 1994).
Roche, "RoActemra 20 mg/ml concentrate for solution for infusion" (EU Prescribing Information) pp. 1-14 (2009).
Rose, et. al., "Mammalian Cell Culture: Process Development Considerations", Handbook of Industrial Cell Culture: Mammalian, Microbial and Plant Cells, Ch. 4, V.A. Vinci and S. R. Parakh, Humana Press, 2003, pp. 69-103.
Saba et al., "A study of immunoglobulin G glycosylation in monoclonal and polyclonal species by electrospray and matrix-assisted laser desorption/ionization mass spectrometry" Anal Biochem 305:16-31 ( 2002).
Sanfeliu, et. al., "Identification of key patterns in the metabolism of hybridoma cells in culture", Enzyme and Microbiol. Technology, 1997, vol. 21, pp. 421-428.

(56) References Cited

OTHER PUBLICATIONS

Schauer, R., "Sialic acids as antigenic determinants of complex carbohydrates" Adv Exp Med Biol 228:47-72 (1988).
Schubert, et. al., "Bioprocess optimization and control: Application of hybrid modelling", Journal of Biotechnology, 1994, vol. 33, pp. 51-68.
Schumpp et al., "Growth Study of Lactate and Ammonia Double-Resistant Clones of HL-60 Cells" Animal Cell Technology pp. 183-185 (1992).
Schwabe, et. al., "Improving an on-line feeding strategy for batch-fed cultures of hybridoma cells by dialysis and 'Nutrient-Split'-feeding", Bioprocess Engineering, 1999, vol. 20, pp. 475-484.
Senger et al. "Optimization of fed-batch parameters and harvest time of CHO cell cultures for a glycosylated product with multiple mechanisms of inactivation", Biotechnology and Bioengineering 98:378-390, 2007.
Staack et al., "Quality requirements for critical assay reagents used in bioanalysis of therapeutic proteins: what bioanalysts should know about their reagents," Bioanalysis 2011, vol. 3, No. 5, pp. 523-534.
Stark et al., "Glucose-Dependent Glycosylation of Secretory Glycoprotein in Mouse Myeloma Cells" Archives of Biochemistry & Biophysics 192:599-609 (1979).
Strube et al., "Carbohydrate Structure of Glycoprotein 52 Encoded by the Polycythemia-inducing Strain of Friend Spleen Focus-forming Virus" The Journal of Biological Chemistry 263:3762-3771 (1988).
Stubenrauch et al., "Generic anti-drug antibody assay with drug tolerance in serum samples from mice exposed to human antibodies," Anal. Biochem. 2012, vol. 430, pp. 193-199.
Stubenrauch et al., "Subset analysis of patients experiencing clinical events of a potentially immunogenic nature in the pivotal clinical trials of tocilizumab for rheumatoid arthritis: Evaluation of an antidrug antibody ELISA using clinical adverse event-driven immunogenicity testing," Clin. Ther. 2010, vol. 32, No. 9, pp. 1597-1609.
Sugiura, T. Enzyme Microb Technol. 22:699-704, 1998.
Tachibana et al., "Changes of monosaccharide availability of human hybridoma lead to alteration of biological properties of human monoclonal antibody" Cytotechnology 16:151-157 (1994).
Taga et al., "Analysis of an antibody pharmaceutical, tocilizumab, by capillary electrophoresis using a carboxylated capillary" J. Sep. Sci. 31:853-858 (2008).
Takuma et al., "Dependence on Glucose Limitation of the pCO 2 Influences on CHO Cell Growth, Metabolism and IgG Production" Biotechnology and Bioengineering 97(6):1479-1488 (Aug. 2007).
Taniguchi et al., "Structures of the sugar chains of rabbit immunoglobulin G: Occurrence of asparagine-linked sugar chains in Fab fragment" Biochem 24:5551-5557 (1985).
Thermofisher Scientific, "Technical Resources: 11965—DMEM, high glucose", 2015, retrieved from http://www.thermofisher.com/us/en/home/technical-resources/media-formulation.8.html on Oct. 13, 2015 (2 pages).
Turco, "Modification of oligosaccharide-lipid synthesis and protein glycosylation in glucose-deprived cells" Arch Biochem Biophys 205(2):330-339 (Dec. 1980).
Venkiteshwaran, A., "Tocilizumab" mAbs 1(5):432-438 (2009).
Vijayalakshmi, "Antibody purification methods" Appl Biochem Biotech 75:93-102 (1998).
Voet & Voet, Excerpts from "Biochemistry", Chapter 16-1, "The Glycolytic Pathway", 2nd edition, Nedah Rose, John Wiley and Sons, 1995, pp. 445, 464, 466.
Werner et al. et al., "Safety and economic aspects of continuous mammalian cell culture" J Biotechnol 22:51-68 (1992).
West, C.M., "Current ideas on the significance of protein glycosylation" Mol Cell Biochem 72:3-20 (1986).
Wong et al., "Impact of Dynamic Online Fed-Batch Strategies on Metabolism, Productivity and N-Glycosylation Quality in CHO Cell Cultures" Biotechnology and Bioengineering 89:164-177 (2005).
Wright and Morrison, "Effect of C2-associated carbohydrate structure on Ig effector function: Studies with chimeric mouse-human IgG1 antibodies in glycosylation mutants of Chinese Hamster Ovary cells" J Immunol 160:3393-3402 (1998).
Wright et al., "In vivo trafficking and catabolism of IgG1 antibodies with Fc associated carbohydrates of differing structure" Glycobiology 10(12):1347-1355 (2000).
Wurm, Florian M., "Production of recombinant protein therapeutics in cultivated mammalian cells", Nature Biotechnology, 2004, vol. 22, pp. 1393-1398.
Xie et al., "Fed-Batch Cultivation of Mammalian Cells for the Production of Recombinant Proteins" (Merck Research Laboratories), Chapter 10, pp. 349-386.
Xie, et. al., "Fed-Batch Cultivation of Animal Cells Using Different Medium Design Concepts and Feeding Strategies", Biotechnol. and Bioengineering, 1994, vol. 43, pp. 1175-1189.
Xie, et. al., "Gamma-Interferon Production and Quality in Stoichiometric Fed-Batch Cultures of Chinese Hamster Ovary (CHO) Cells under Serum-Free Conditions", Biotechnol. and Bioengineering, 1997, vol. 56, pp. 577-582.
Xie, et. al., "Integrated approaches to the design of media and feeding strategies for fed-batch cultures of animal cells", TIBTECH, 1997, vol. 15, pp. 475-484.
Yamané, et. al., "Fed-batch Techniques in Microbial Processes", Adv. Biochem. Eng. Biotechnol., 1984, vol. 30, pp. 147-194.
Youings et al., "Site-specific glycosylation of human immunoglobulin G is altered in four rheumatoid arthritis patients" Biochem J 314:621-630 (1996).
Yu et al., "Production, characterization, and pharmacokinetic properties of antibodies with N-linked mannose-5 glycans" MAbs 4(4):475-487 (Jul. 2012).
Zeng et al., "Cell Culture Kinetics and Modeling" GBF National Research Institute for Biotechnology, Braunschweig, Chapter 9, pp. 299-348.
Zeng, "Mathematical Modeling and Analysis of Glucose and Glutamine Utilization and Regulation in Cultures of Continuous Mammalian Cells" Biotechnology and Bioengineering 47:334-346 (1995).
Zeng, et. al., "Variation of Stoichiometric Ratios and Their Correlation for Monitoring and Control of Animal Cell Cultures", Biotechnol. Prog., 1998, vol. 14, pp. 434-441.
Zhou et al., "On-Line Characterization of Hybridoma Cell Culture Process" Biotechnology and Bioengineering 44:170-177 (1994).
Zhou, et. al., "Alteration of mammalian cell metabolism by dynamic nutrient feeding", Cytotechnology, 1997, vol. 24, pp. 99-108.
Zhou, et. al., "High Viable Cell Concentration Fed-Batch Cultures of Hybridoma Cells Through On-Line Nutrient Feeding", Biotechnology and Bioengineering, 1995, vol. 46, pp. 579-587.
Zielke et al., "Reciprocal Regulation of Glucose and Glutamine Utilization by Cultured Human Dipoid Fibroblasts" Journal of Cellular Physiology 95:41-48 (1978).
Zuckier et al., "Chimeric human-mouse IgG antibodies with shuffled constant region exons demonstrate that multiple domains contribute to in vivo half-life" Cancer Res 58:3905-3908 (1998).
Hoffmann et al., "PK modulation of haptenylated peptides via non-covalent antibody complexation," Journal of Controlled Release, Oct. 10, 2013 (Epub Jun. 22, 2013), 171(1):48-56.
Maraveyas et al., "Improving Tumour Targeting and Decreasing Normal Tissue Uptake by Optimizing the Stoichiometry of a Two-Step Biotinylated-Antibody/Streptavidin-Based Targeting Strategy: Studies in a Nude Mouse Xenograft Model," Int. J. Cancer, Nov. 23, 1998, 78(5):610-617.

* cited by examiner

INTERFERENCE-SUPPRESSED IMMUNOASSAY TO DETECT ANTI-DRUG ANTIBODIES IN SERUM SAMPLES

Herein is reported an interference-suppressed immunoassay to detect anti-drug antibodies in serum samples from patients treated with an anti-inflammatory antibody and uses thereof.

BACKGROUND OF THE INVENTION

The clinical development of novel therapeutic antibodies requires the evaluation of their potential immunogenicity by appropriate assays (Kaliyaperumal, A. and Jing, S., Curr. Pharm. Biotechnol. 10 (2009) 352-358). The anti-drug antibody (ADA) testing usually involves a two tier approach: (1) assays for ADA detection and (2) assays for ADA characterization. ADA detection assays include screening and specificity confirmation (confirmatory) assays. Microtiter plate-based enzyme-linked immunosorbent assays (ELISAs) are still the most widely used format to screen for ADAs due to their high-throughput efficiency, relative simplicity and high sensitivity (Geng, D., et al., J. Pharm. Biomed. Anal. 39 (2005) 364-375). ADA ELISAs are most often designed in a bridge format which provides high selectivity, detection of all isotypes and pan-species ADA detection capability (Mire-Sluis, A. R., et al., J. Immunol. Methods 289 (2004) 1-16).

A bridging ELSA has been developed and used as a screening and confirmation ADA assay for the anti-IL6R antibody tocilizumab (Stubenrauch, K., et al., Clin. Ther. 32 (2010) 1597-1609).

Stubenrauch, K., et al. report a generic anti-drug antibody assay with drug tolerance in serum samples from mice exposed to human antibodies (Anal. Biochem. 430 (2012) 193-199). Bourdage, J. S., et al. report the effect of double antigen bridging immunoassay format on antigen coating concentration dependence and implications for designing immunogenicity assays for monoclonal antibodies (J. Pharm. Biochem. Anal. 39 (2005) 685-690). Mikulskis, A., et al. report solution ELISA as a platform of choice for development of robust, drug tolerant immunogenicity assays in support of drug development (J. Immunol. Meth. 365 (2010) 38-49). Pan, J., et al. report the comparison of the NIDSA® rapid assay with ELISA methods in immunogenicity testing of two biotherapeutics (J. Pharm. Tox. Meth. 63 (2010) 150-159.

Qiu, Z. J., et al. report a novel homogeneous biotin-digoxigenin based assay for the detection of human anti-therapeutic antibodies in autoimmune serum (J. Immunol. Meth. 362 (2010) 101-111).

SUMMARY OF THE INVENTION

Herein is reported a bridging enzyme linked immunosorbent assay (bridging ELISA) that can be used as screening, confirmation and follow-up assay for the detection of anti-drug antibodies (ADA) in serum containing samples of patients treated with a therapeutic antibody. The assay as reported herein is especially useful if the serum containing sample is from a patient with an autoimmune diseases such as rheumatoid arthritis (RA).

The assay as reported herein shows an improved tolerance with respect to the amount of therapeutic antibody in the sample to be analyzed (increased drug tolerance of the ADA ELISA) and at the same time the number of false positive assay results is reduced.

It has been found that with the assay as reported herein interferences by free drug and by rheumatoid factors (RF) can be minimized.

This assay is especially useful if the sample contains antibodies other than the anti-drug antibody in question which can interfere in immunoassays for the detection of anti-drug antibodies and, thus, would account for a false positive immunoassay result.

In one embodiment the methods as reported herein are used for the determination of anti-drug antibodies of drug antibodies used for an anti-inflammatory therapy.

The increased drug tolerance was achieved by a synergistic interaction of 1) increasing the concentration of biotinylated and digoxigenylated capture and tracer reagents; 2) simultaneous, instead of sequential incubation of the serum sample with the capture and tracer reagents; 3) a prolonged incubation time; 4) use of homogenously mono-coupled capture and tracer reagents; and 5) use of an increased serum matrix content.

The interference from rheumatoid factors can be suppressed by addition of oligomeric human immunoglobulin G (IgG) as an additive.

The drug tolerance of the interference-suppressed ADA assay as reported herein is at least 10-fold higher than that of assays known in the art.

One aspect as reported herein is an enzyme linked immunosorbent assay for the detection of anti-drug antibodies against a drug antibody in a sample comprising a capture drug antibody and a tracer drug antibody, wherein
  a) the capture drug antibody and the tracer drug antibody are employed in a concentration of more than 0.5 µg/ml,
  b) the sample is incubated simultaneously with the capture drug antibody and the tracer drug antibody for 4 to 24 hours,
  c) the capture drug antibody and the tracer drug antibody are derivatized via a single lysine residue,
  d) the sample comprises 7.5% serum or more, and
  e) oligomeric human IgG is added to the sample prior to the incubation with the capture drug antibody and the tracer drug antibody.

One aspect as reported herein is an enzyme linked immunosorbent assay for the detection of anti-drug antibodies against a drug antibody in a sample of a rheumatoid arthritis patient comprising a capture drug antibody and a tracer drug antibody, wherein
  a) the capture drug antibody and the tracer drug antibody have a concentration of 0.5 µg/ml or more in the enzyme linked immunosorbent assay,
  b) the sample is incubated simultaneously with the capture drug antibody and the tracer drug antibody for 0.5 to 24 hours,
  c) the capture drug antibody is a 1:1 conjugate of the capture drug antibody and a first component of a specific binding pair and the tracer drug antibody is a 1:1 conjugate of the tracer drug antibody and a detectable label,
  d) the sample comprises 1% serum or more, and
  e) oligomeric human IgG is added to the sample prior to the incubation with the capture drug antibody and the tracer drug antibody.

In one embodiment the sample comprises 5% serum or more. In one embodiment the sample comprises 7.5% serum or more.

In one embodiment the sample comprises anti-drug antibodies and rheumatoid factors.

In one embodiment the drug antibody is an antibody for the treatment of an inflammatory disease. In one embodiment the antibody for the treatment of an inflammatory disease is an antibody for the treatment of an autoimmune disease. In one embodiment the autoimmune disease is rheumatoid arthritis or juvenile arthritis or osteoarthritis or Castleman's disease.

In one embodiment the drug antibody is an antibody for the treatment of cancer. In one embodiment the antibody is for the treatment of myeloma or plasmacytoma.

In one embodiment the drug antibody is an antibody against the IL-6 receptor (anti-IL6R antibody), or against the IGF-1 receptor (anti-IGF1R antibody), or the IL-13 receptor 1 alpha (anti-IL13R1 alpha antibody), or against Ox40L (anti-Ox40L antibody), or against tumor necrosis factor alpha (anti-TNFalpha antibody). In one embodiment the drug antibody is an anti-IL6R antibody. In one embodiment the anti-IL6R antibody is tocilizumab.

In one embodiment the capture drug antibody is conjugated to a solid phase. In one embodiment the conjugation of the capture drug antibody to the solid phase is performed via a specific binding pair. In one embodiment the specific binding pair (first component/second component) is selected from Streptavidin or Avidin/biotin, or antibody/antigen (see, for example, Hermanson, G. T., et al., Bioconjugate Techniques, Academic Press, 1996), or lectin/polysaccharide, or steroid/steroid binding protein, or hormone/hormone receptor, or enzyme/substrate, or IgG/Protein A and/or G.

In one embodiment the capture drug antibody is conjugated to biotin (as first component of a specific binding pair). In this case the conjugation to the solid phase is performed via immobilized Avidin or Streptavidin.

In one embodiment the tracer drug antibody is conjugated to a detectable label. In one embodiment the tracer drug antibody is conjugated to the detectable label via a specific binding pair. In one embodiment the specific binding pair (first component/second component) is selected from Streptavidin or Avidin/biotin, or antibody/antigen (see, for example, Hermanson, G. T., et al., Bioconjugate Techniques, Academic Press, 1996), or lectin/polysaccharide, or steroid/steroid binding protein, or hormone/hormone receptor, or enzyme/substrate, or IgG/Protein A and/or G.

In one embodiment the tracer drug antibody is conjugated to digoxigenin (as detectable label). In this case linking to the detectable label is performed via an antibody against digoxigenin.

In one embodiment the capture drug antibody and the tracer drug antibody have a concentration in the enzyme linked immunosorbent assay (ELISA) of about 0.5 µg/ml to about 10 µg/ml. In one embodiment the capture drug antibody and the tracer drug antibody have a concentration of more than 0.5 µg/ml to less than 10 µg/ml. In one embodiment the capture drug antibody and the tracer drug antibody have a concentration of about 1 µg/ml to about 5 µg/ml. In one embodiment the capture drug antibody and the tracer drug antibody have a concentration of about 1.4 µg/ml to about 1.8 µg/ml. In one embodiment the capture drug antibody and the tracer drug antibody have a concentration of about 1.45 µg/ml to about 1.6 µg/ml. In one preferred embodiment the capture drug antibody and the tracer drug antibody have a concentration of about 1.5 µg/ml.

In one embodiment the incubation time is at least 6 hours. In one embodiment the incubation time is at least 12 hours. In one embodiment the incubation time is at least 16 hours. In one embodiment the incubation time is at most 24 hours.

In one embodiment the incubation time is between 4 hours and 24 hours. In one embodiment the incubation time is between 6 hours and 24 hours. In one embodiment the incubation time is between 12 hours and 24 hours. In one preferred embodiment the incubation time is between 12 hours and 20 hours. In one embodiment the incubation time is between 14 hours and 18 hours. In one embodiment the incubation time is about 16 hours.

In one embodiment the sample comprises 1% to 20% serum. In one embodiment the sample comprises about 10% serum.

In one embodiment the oligomeric human IgG is added to a final concentration of 10 µg/mL to 1000 µg/mL. In one embodiment the oligomeric human IgG is added to a final concentration of 15 µg/mL to 500 µg/mL. In one embodiment the oligomeric human IgG is added to a final concentration of 20 µg/mL to 250 µg/mL. In one embodiment the oligomeric human IgG is added to a final concentration of 25 µg/mL to 100 µg/mL. In one preferred embodiment the oligomeric human IgG is added to a final concentration of about 50 µg/mL.

One aspect as reported herein is an enzyme linked immunosorbent assay for the detection of anti-drug antibodies against a drug antibody in a sample of a rheumatoid arthritis patient comprising a capture drug antibody and a tracer drug antibody, wherein
  a) the capture drug antibody and the tracer drug antibody have a concentration of about 1.5 µg/ml in the enzyme linked immunosorbent assay,
  b) the sample is incubated simultaneously with the capture drug antibody and the tracer drug antibody for 14 to 16 hours,
  c) the capture drug antibody is a 1:1 conjugate of the capture drug antibody and biotin via a lysine residue of the capture drug antibody and the tracer drug antibody is a 1:1 conjugate of the tracer drug antibody and digoxigenin via a lysine residue of the tracer drug antibody,
  d) the sample comprises 1% to 20% serum, and
  e) oligomeric human IgG is added to the sample to a final concentration of 25 µg/mL to 100 µg/mL prior to the incubation with the capture drug antibody and the tracer drug antibody.

One aspect as reported herein is the use of oligomeric human IgG for the capture of rheumatoid factors in an anti-drug antibody ELISA.

One aspect as reported herein is a method of treating an individual having a disease comprising administering to the individual an effective amount of a therapeutic antibody (drug) and determining the presence of anti-drug antibodies with an assay as reported herein.

One aspect as reported herein is a method of treating an individual having an inflammatory disease comprising administering to the individual an effective amount of an anti-IL6R antibody (drug) and determining the presence of anti-anti-IL6R antibody antibodies (anti-drug antibodies) with an assay as reported herein.

In one embodiment the inflammatory disease is an autoimmune disease. In one embodiment the autoimmune disease is selected from rheumatoid arthritis, juvenile arthritis, osteoarthritis, or Castleman's disease.

In one embodiment the inflammatory disease is mesangial proliferative glomerulonephritis.

One aspect as reported herein is a method of treating an individual having plasmacytoma comprising administering to the individual an effective amount of an anti-IL6R antibody (drug) and determining the presence of anti-anti-IL6R antibody antibodies (anti-drug antibodies) with an assay as reported herein.

One aspect as reported herein is a method of treating an individual having myeloma comprising administering to the individual an effective amount of an anti-IL6R antibody (drug) and determining the presence of anti-anti-IL6R antibody antibodies (anti-drug antibodies) with an assay as reported herein.

One aspect as reported herein is a method of inhibiting IL6R activity in an individual comprising administering to the individual an effective amount of an anti-IL6R antibody to inhibit IL6R activity and determining the presence of anti-anti-IL6R antibody antibodies (anti-drug antibodies) with an assay as reported herein.

DEFINITIONS

Figure 1:
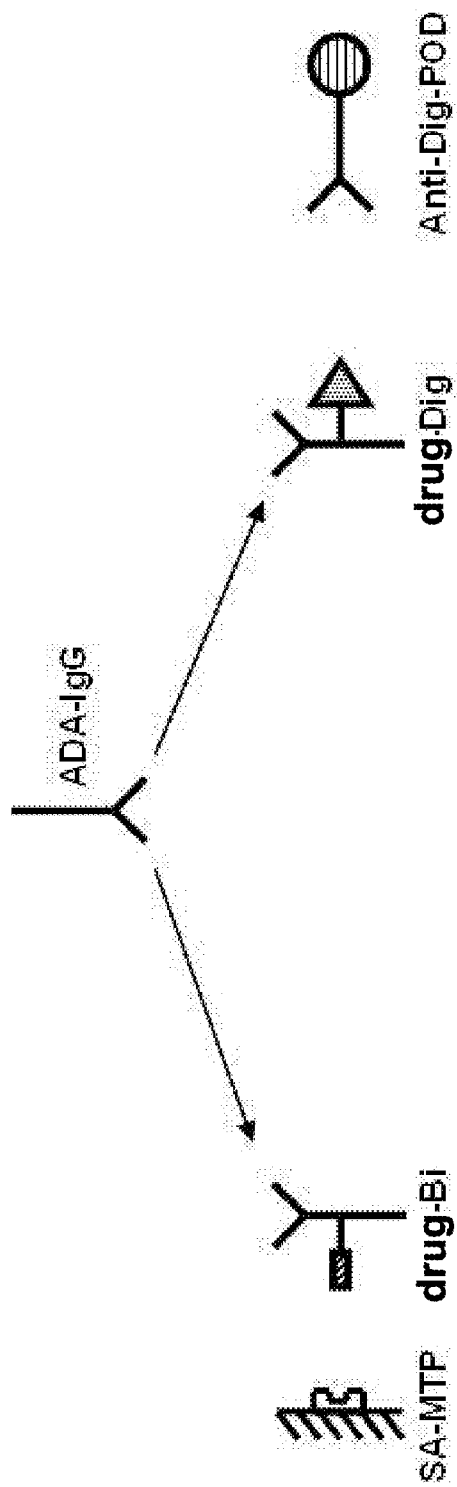
FIG. 1 Assay principle of the drug-tolerant anti-drug antibody assay exemplified for anti-IL6R antibody tocilizumab.

The term "1:1 conjugate" denotes a conjugate consisting of exactly two entities joined/conjugated to each other via a single covalent bond. For example the term "1:1 conjugate of the capture drug antibody and a first component of a specific binding pair" denotes a chemical conjugate consisting of exactly one molecule of the capture drug antibody covalently conjugated via a single chemical bond to exactly one molecule of the first component of a specific binding pair. Likewise the term "1:1 conjugate of the tracer drug antibody and a detectable label" denotes a chemical conjugate consisting of exactly one molecule of the tracer drug antibody covalently conjugated via a single chemical bond to exactly one detectable label molecule.

The term "drug antibody" according to the invention denotes an antibody which can be administered to an individual, so that a sample of said individual is suspected to comprise said drug antibody after administration. A drug antibody is an antibody that is intended to be administered to a human for a therapeutic purpose. Within one assay as reported herein the drug antibody, the capture drug antibody and the tracer drug antibody comprise the "same" antibody molecule, e.g. recombinantly produced with the same expression vector and comprising the same amino acid sequence. Drug antibodies (therapeutic monoclonal antibodies) are being used widely for the treatment of various diseases such as oncological diseases (e.g. hematological and solid malignancies including non-Hodgkin's lymphoma, breast cancer, and colorectal cancer) or inflammatory diseases. Such antibodies are reported, for example, by Levene, A. P., et al., Journal of the Royal Society of Medicine 98 (2005) 145-152; Groner, B., et al., Curr. Mol. Meth. 4 (2004) 539-547; and Harris, M., Lancet Oncol. 5 (2004) 292-302.

In one embodiment the drug antibody is an antibody which is useful for the treatment of an inflammatory disease, i.e. an anti-inflammatory antibody, such as an anti-IL-6 receptor antibody, or an anti-IGF-1 receptor antibody, or an anti-IL-13 receptor 1 alpha antibody.

An example (preferably monoclonal) drug antibody is an antibody against the IL-6 receptor (anti IL6R antibody). Such an antibody is, for example, reported by Mihara, et al., Clin. Immunol. 98 (2001) 319-326; Nishimoto, N., et al, Blood 106 (2005) 2627-2632, in clinical trial NCT00046774, or in WO 2004/096274.

An example (preferably monoclonal) drug antibody is an antibody against the IGF-1 receptor (anti IGF1R antibody). Such an antibody is, for example, reported in WO 2004/087756 or in WO 2005/005635.

An example (preferably monoclonal) drug antibody is an antibody against the IL-13 receptor alpha (anti IL13R1alpha antibody). Antibodies against IL-13R1alpha are known from, e.g., WO 96/29417, WO 97/15663, WO 03/080675, Graber, P., et al., Eur. J. Immunol. 28 (1998) 4286-4298; Poudrier, J., et al., J. Immunol. 163 (1999) 1153-1161; Poudrier, J., et al., Eur. J. Immunol. 30 (2000) 3157-3164; Aikawa, M., et al., Cytokine 13 (2001) 75-84, and are commercially available from, e.g., R&D Systems Inc. USA. Further exemplary antibodies against IL-13R1alpha are reported in WO 2006/072564.

The term "drug antibody used for an anti-inflammatory therapy" as used herein denotes a drug antibody that is directed against a cell surface receptor that mediates inflammation. Such receptors are for example the IL-6 receptor, or the IGF-1 receptor, or the IL-13a receptor 1. If a sample from a patient, which is treated with such an anti-inflammatory drug antibody, is analyzed, it has to be determined, whether the positive result of the method is based on a true anti-drug antibody (true positive result) or on an antibody other than an anti-drug antibody of the sample (false positive result). An example of such a case is a sample from a patient, who has an autoimmune disease such as rheumatism, and, thus, a sample obtained from said patient contains so called "rheumatoid factors". The term "rheumatoid factors" as used herein denotes antibodies binding to human IgG, to be more precisely to the Fc-region of human IgG. In most cases these "rheumatic factors" are oligomeric binding molecules.

The term "anti-drug antibody" as used herein denotes an antibody, which is directed against, i.e. binds to, an antigenic region of a drug antibody. This antigenic region may be the variable region, a CDR, the constant region, or the glyco-structure of the drug antibody. In one embodiment the anti-drug antibody is directed against a CDR of the drug antibody or a secondary modification of the drug antibody resulting from the recombinant production of the drug antibody in recombinant cells, such as, CHO cells, HEK cells, Sp2/0 cells, or BHK cells. Generally anti-drug antibodies are directed against an antigenic region of a drug antibody that is recognized by the immune system of an animal to which the drug antibody is administered. The above described antibodies are termed "specific anti-drug antibodies".

Drug antibodies are designed to comprise as few as possible antigenic regions. For example, drug antibodies intended for the use in humans are humanized prior to the application to a human patient in order to minimize the generation of an immune response against the drug antibody. This immune response would be in the form of anti-drug antibodies (ADAs), which are directed against the non-human parts of such a humanized drug antibodies, such as e.g. the complementary determining regions in the variable domains (see e.g. Pan, Y., et al., FASEB J. 9 (1995) 43-49).

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:
  (a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));
  (b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, Md. (1991));
  (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
  (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat.

Antibodies contain a number of reactive moieties, such as, for example, amino groups (lysins, alpha-amino groups), thiol groups (cystins, cysteine, and methionine), carboxylic acid groups (aspartic acid, glutamic acid) and sugar-alcoholic groups. These can be employed for coupling to a binding partner like a surface, a protein, a polymer (such as e.g. PEG, Cellulose or Polystyrol), an enzyme, or a member of a binding pair (see e.g. Aslam M. and Dent, A., Bioconjuation MacMillan Ref. Ltd. (1999) 50-100).

The term "anti-idiotypic antibody" denotes an antibody, which specifically binds to a binding specificity, such as e.g. a binding site, of a parent antibody, i.e. an anti-idiotypic antibody is directed e.g. against an antigen binding site of a parent antibody.

In one embodiment the anti-idiotypic antibody specifically binds to one or more of the CDRs of the parent antibody.

In one embodiment the parent antibody is a therapeutic antibody. In one embodiment the parent antibody is a multispecific antibody. In one embodiment the parent antibody is a bispecific antibody.

One of the most common reactive groups of proteins is the aliphatic ε-amine of the amino acid lysine. In general, nearly all antibodies contain abundant lysine residues. Lysine amines/amino groups are reasonably good nucleophiles above pH 8.0 ($pK_a$=9.18) and therefore react easily and cleanly with a variety of reagents to form stable bonds.

Another common reactive group in antibodies is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, proteins with these groups often exist with them in their oxidized form as disulfide groups or disulfide bonds.

In addition to cystine and cysteine, some proteins also have the amino acid methionine, which is containing sulfur in a thioether linkage. The literature reports the use of several thiolating crosslinking reagents such as Traut's reagent (2-iminothiolane), succinimidyl (acetylthio) acetate (SATA), or sulfosuccinimidyl 6-[3-(2-pyridyldithio) propionamido] hexanoate (Sulfo-LC-SPDP) to provide efficient ways of introducing multiple sulfhydryl groups via reactive amino groups.

Reactive esters, particularly N-hydroxysuccinimide (NHS) esters, are among the most commonly employed reagents for modification of amine groups. The optimum pH for reaction in an aqueous environment is pH 8.0 to 9.0.

Isothiocyanates are amine-modification reagents and form thiourea bonds with proteins. They react with protein amines in aqueous solution (optimally at pH 9.0 to 9.5).

Aldehydes react under mild aqueous conditions with aliphatic and aromatic amines, hydrazines, and hydrazides to form an imine intermediate (Schiff's base). A Schiff's base can be selectively reduced with mild or strong reducing agents (such as sodium borohydride or sodium cyanoborohydride) to derive a stable alkyl amine bond.

Other reagents that have been used to modify amines are acid anhydrides. For example, diethylenetriaminepentaacetic anhydride (DTPA) is a bifunctional chelating agent that contains two amine-reactive anhydride groups. It can react with N-terminal and ε-amine groups of proteins to form amide linkages. The anhydride rings open to create multivalent, metal-chelating arms able to bind tightly to metals in a coordination complex.

The term "sample" includes, but is not limited to, any quantity of a substance from a living thing or formerly living thing. Such living things include, but are not limited to, humans, mice, monkeys, rats, rabbits, and other animals. In one embodiment the sample is obtained from a monkey, especially a cynomolgus monkey, or a rabbit, or a mouse or rat. Such substances include, but are not limited to, in one embodiment whole blood, serum, or plasma from an individual, which are the most widely used sources of sample in clinical routine.

The term "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component is distinguished from inert solid surfaces in that a "solid phase" contains at least one moiety on its surface, which is intended to interact with a substance in a sample. A solid phase may be a stationary component, such as a tube, strip, cuvette or microtiter plate, or may be non-stationary components, such as beads and microparticles. A variety of microparticles that allow both non-covalent and covalent attachment of proteins and other substances can be used. Such particles include polymer particles such as polystyrene and poly (methylmethacrylate); gold particles such as gold nanoparticles and gold colloids; and ceramic particles such as silica, glass, and metal oxide particles. See for example Martin, C. R., et al., Analytical Chemistry-News & Features, 70 (1998) 322A-327A, or Butler, J. E., Methods 22 (2000) 4-23.

From chromogens (fluorescent or luminescent groups and dyes), enzymes, NMR-active groups, metal particles, or haptens, such as digoxigenin, the detectable label is selected in one embodiment. In one embodiment the detectable label is digoxigenin. The detectable label can also be a photoactivatable crosslinking group, e.g. an azido or an azirine group. Metal chelates which can be detected by electrochemiluminescense are also in one embodiment signal-emitting groups, with particular preference being given to ruthenium chelates, e.g. a ruthenium $(bispyridyl)_3^{2+}$ chelate. Suitable ruthenium labeling groups are described, for example, in EP 0 580 979, WO 90/05301, WO 90/11511, and WO 92/14138.

The principles of different immunoassays are described, for example, by Hage, D. S. (Anal. Chem. 71 (1999) 294R-304R). Lu, B., et al. (Analyst 121 (1996) 29R-32R) report the orientated immobilization of antibodies for the use in immunoassays. Avidin-biotin-mediated immunoassays are reported, for example, by Wilchek, M., and Bayer, E. A., in Methods Enzymol. 184 (1990) 467-469.

DETAILED DESCRIPTION OF THE INVENTION

Herein reported is an interference-suppressed anti-drug antibody assay using serum samples with increased tolerance to free therapeutic antibody and increased resistance to rheumatoid factor interference.

The principle of an anti-drug antibody assay is the capture of anti-drug antibodies (ADAs) in a complex with digoxigenylated drug (drug-Dig) and biotinylated drug (drug-Bi) (e.g. tocilizumab (TCZ-Dig and TCZ-Bi, respectively)), the latter one leading to immobilization onto a streptavidin-coated plate (SA-MTP). The ADA/drug-Dig complex bound to drug-Bi on the SA-MTP is detected by an anti-digoxigenin antibody horseradish peroxidase enzyme conjugate (anti-Dig-HRP). The horseradish peroxidase (HRP) catalyzes a color reaction of the substrate ABTS. The color intensity is proportional to the concentration of the analyte. The general principle of an anti-drug antibody assay is shown in FIG. 1.

It has been found that without alteration of the general assay principle the drug and rheumatoid factor tolerance of a conventional anti-drug antibody assay could be increased by
1) increasing the concentration of biotinylated and digoxigenylated capture and tracer reagents;
2) simultaneous, instead of sequential incubation of the serum sample with the capture and tracer reagents;
3) prolonged incubation of the serum sample with the capture and tracer reagents;
4) use of homogenous capture and tracer reagents instead of a heterogeneously coupled mixture;
5) use of an increased serum matrix;
6) inclusion of oligomeric IgG as assay additive; and
7) use of mono biotinylated capture and mono digoxigenylated tracer antibody.

These measures provided for a synergistic effect.

The above measures lead to an interference-suppressed drug-tolerant anti-drug antibody assay for the detection of anti-drug antibodies against a therapeutic drug antibody.

Figure 2:
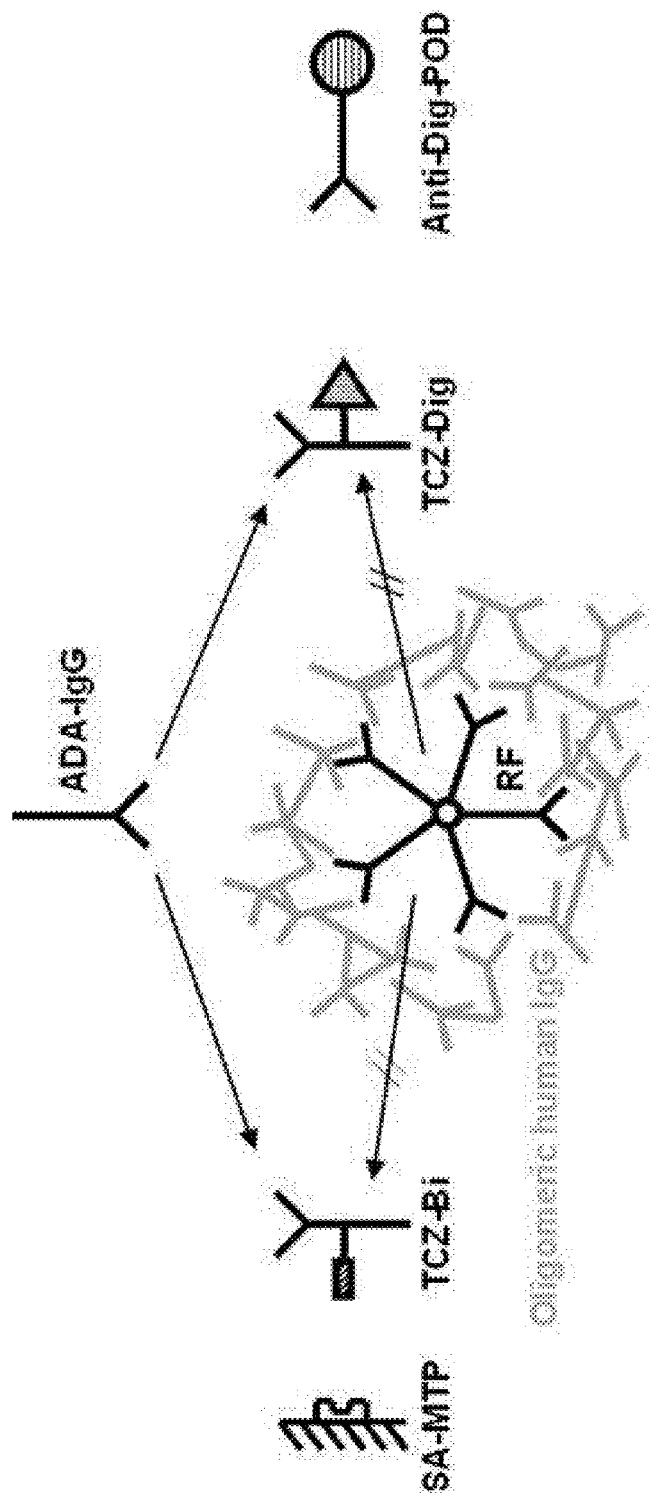
FIG. 2 Assay principle of the interference-suppressed anti-drug antibody assay for anti-IL6R antibody tocilizumab.

The general principle of the interference-suppressed drug-tolerant anti-drug antibody assay as reported herein is shown in FIG. 2 exemplified for the anti-IL6R antibody tocilizumab.

With the assay setup as reported herein drug tolerance of the ADA assay was increased at least 10-fold in serum samples from patients compared to a conventional anti-drug antibody assay. At the same time susceptibility to rheumatoid factors leading to false-positive assay results was also decreased.

The therapeutic anti-inflammatory antibody tocilizumab (TCZ) is a recombinant humanized monoclonal antibody directed against the interleukin-6 receptor. It has been shown to be effective in clinical studies of rheumatoid arthritis (Ohsugi, Y. and Kishimoto, T., Expert Opin. Biol. Ther. 8 (2008) 669-681). The ADA screening and confirmation assay used in these studies shows sufficient drug tolerance for typical TCZ serum concentrations reached at steady state using an intravenous dosing regimen.

But different routes of administration, such as subcutaneous administration, more frequent administration, and new indications in children might result in higher TCZ serum concentrations at steady state.

Additionally, for example, rheumatoid factors (RF) are often significantly increased in patients with autoimmune diseases, such as e.g. rheumatoid arthritis patients. RFs demonstrate a preferential binding to aggregated gamma globulins and are involved in the clearance mechanism of immune complexes in vivo (Tatarewicz, S., et al., J. Immunol. Methods. 357 (2010) 10-16). RFs are preferentially of the pentameric immunoglobulin M (IgM) isotype (Artandi, S. E., et al., Proc. Natl. Acad. Sci. USA 89 (1991) 94-98) and can non-specifically bind with multivalency and medium affinity to the constant part of the therapeutic antibody leading to a false positive result in an ADA assay. For example, affinity purified rabbit anti-human IgM antibody was included in the sample diluent to overcome the cross reactive IgM antibody interference in RA samples (see e.g. Araujo, J., et al., J. Pharm. Biomed. Anal., 55 (2011) 1041-1049).

It has been found that unspecific binding of RF present in the serum sample to the therapeutic antibody could be prevented by adding oligomeric human IgG to the sample prior to performing the ADA assay. The added oligomeric IgG provides for additional targets for the RF and at most eliminates the interference of RF in the ADA assay as reported herein.

In the following the interference-suppressed ADA assay as reported herein is exemplified by the analysis of serum samples of tocilizumab (TCZ) treated rheumatoid arthritis patients.

Measures to increase drug tolerance of the conventional anti-drug antibody assay for detecting anti-drug antibodies against the anti-IL6R antibody tocilizumab were
1) increasing the concentration of biotinylated and digoxigenylated TCZ (e.g. from 0.5 µg/mL to 1.5 µg/mL);
2) simultaneous incubation of the serum sample with TCZ-Bi and TCZ-Dig;
3) prolonged incubation of the serum sample with TCZ-Bi and TCZ-Dig (e.g. from 1 hour to 16 hours);

4) use of only lysine-coupled TCZ-Bi and TCZ-Dig reagents instead of a mixture of lysine- and carbohydrate-coupled reagents;
5) use of an increased serum matrix content; and
6) addition of oligomeric human IgG to the sample prior to incubation TCZ-Bi and TCZ-Dig.

Drug Tolerance

Concentrations of the anti-IL6R antibody tocilizumab to be detected in clinical samples are 0.5 µg/mL or higher, often in the range of from 1 µg/mL to 10 µg/mL.

The drug tolerance of the conventional anti-drug antibody assay was evaluated by determining the highest TCZ concentration at which a given concentration of positive control ADA can be detected above the cut-point. Table 1 presents a summary of the results.

TABLE 1

Determination of drug (tocilizumab) tolerance in the conventional anti-drug antibody ELISA. Left-aligned signal values are below the plate-specific cut-point of 0.136 AU.

| ADA [ng/mL] | tocilizumab [µg/mL] | | | | | |
|---|---|---|---|---|---|---|
| | 6250 | 1250 | 250 | 50 | 10 | 0 |
| | signal mean [AU] | | | | | |
| 100000 | 0.049 | 0.109 | 0.949 | 3.094 | 3.169 | 3.144 |
| 10000 | 0.050 | 0.062 | 0.156 | 1.265 | 3.117 | 3.387 |
| 1000 | 0.052 | 0.058 | 0.071 | 0.189 | 0.865 | 2.141 |
| 500.0 | 0.051 | 0.057 | 0.065 | 0.120 | 0.448 | 1.282 |
| 250.0 | 0.055 | 0.060 | 0.065 | 0.092 | 0.255 | 0.703 |
| 125.0 | 0.056 | 0.060 | 0.064 | 0.076 | 0.157 | 0.385 |
| 62.5 | 0.056 | 0.060 | 0.062 | 0.067 | 0.108 | 0.226 |
| 0 | 0.059 | 0.061 | 0.062 | 0.062 | 0.060 | 0.071 |

An ADA concentration of 125 ng/mL was detected and tested positive in the presence of 10 µg/mL TCZ.

The drug tolerance of the interference-suppressed drug-tolerant anti-drug antibody assay as reported herein was evaluated by determining the highest TCZ concentration at which a given concentration of positive control ADA can be detected above the cut-point. Table 2 presents a summary of the results.

TABLE 2

Determination of drug (tocilizumab) tolerance in the interference-suppressed drug-tolerant anti-drug antibody ELISA as reported herein. Left-aligned signal values are below the plate-specific cut-point of 0.045 AU.

| ADA [ng/mL] | tocilizumab [µg/mL] | | | | | |
|---|---|---|---|---|---|---|
| | 100 | 30 | 10 | 3 | 1 | 0 |
| | signal mean [AU] | | | | | |
| 10,000 | 0.948 | 2.263 | 3.266 | 3.536 | 3.146 | 3.272 |
| 3,000 | 0.310 | 0.943 | 1.956 | >3.5 | 2.860 | 3.161 |
| 1,000 | 0.119 | 0.364 | 0.789 | 1.051 | 1.180 | 2.292 |
| 300 | 0.055 | 0.133 | 0.280 | 0.376 | 0.426 | 0.857 |
| 100 | 0.033 | 0.057 | 0.105 | 0.144 | 0.163 | 0.310 |
| 30 | 0.027 | 0.036 | 0.051 | 0.063 | 0.068 | 0.113 |
| 10 | 0.022 | 0.025 | 0.032 | 0.039 | 0.040 | 0.056 |
| 0 | 0.024 | 0.023 | 0.026 | 0.027 | 0.027 | 0.027 |

In the interference-suppressed drug-tolerant anti-drug antibody ELISA as reported herein a very low ADA concentration of 30 ng/mL was detected and tested positive in the presence of 10 µg/mL TCZ. Furthermore ADA concentrations of 100 ng/mL and 300 ng/mL show a drug antibody tolerance of 30 µg/ml and even 100 µg/mL, respectively.

Figure 4:
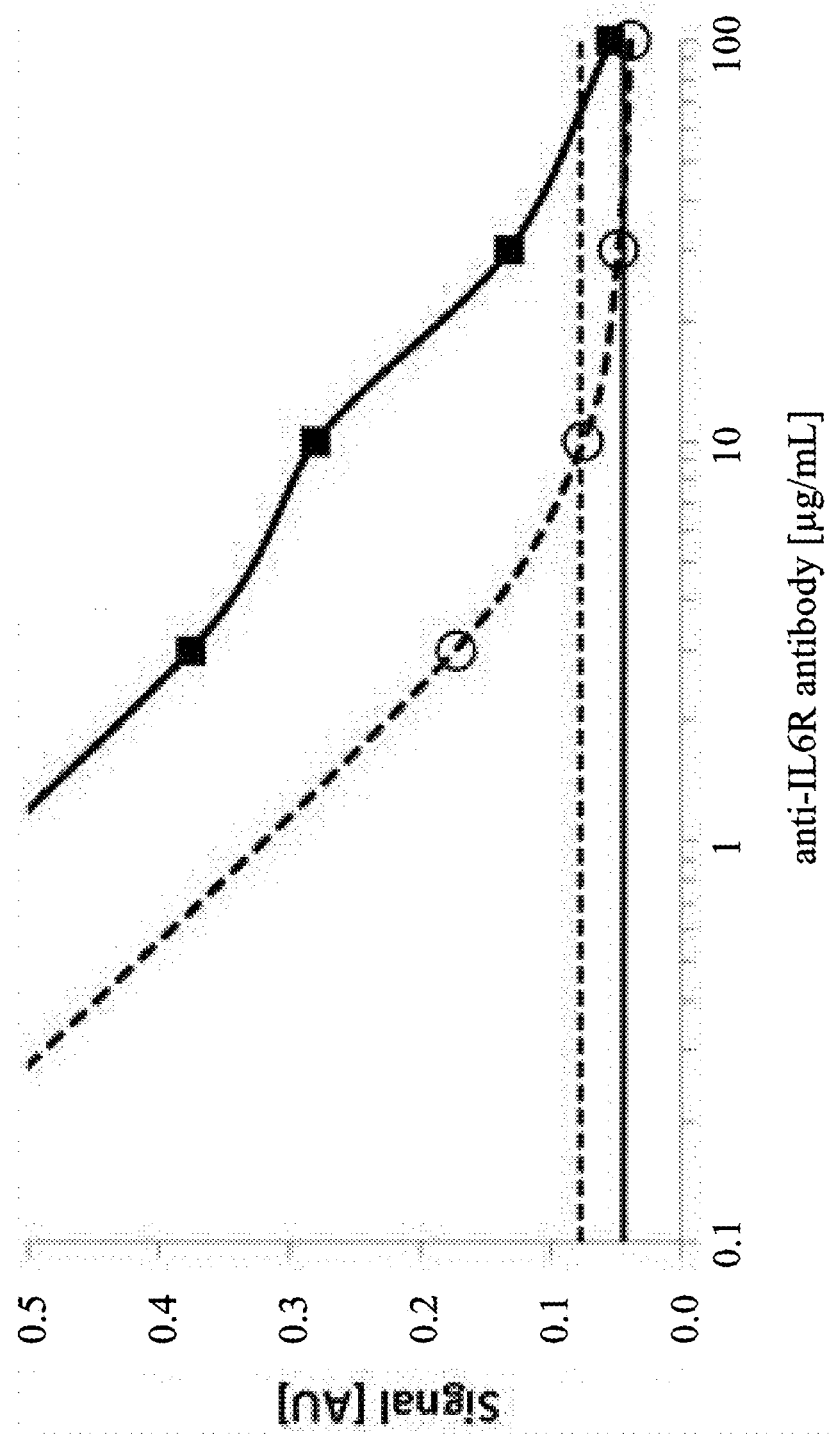
FIG. 4 Comparison of drug tolerance in the two-step anti-drug antibody ELISA and in the interference-suppressed anti-drug antibody ELISA as reported herein for the anti-IL6R antibody tocilizumab; signal of 300 ng/mL anti-drug antibody in presence of increasing amounts of drug are shown; dotted line: CP conventional assay; solid line: CP interference-suppressed assay as reported herein; dotted line with circles: conventional assay; solid line with squares: interference-suppressed assay as reported herein.

In comparison with the same experiments conducted with the previously used, two-step conventional anti-drug antibody ELISA for tocilizumab revealed an at least 10-fold higher drug tolerance with the interference-suppressed assay (see also FIG. 4 for 300 ng/mL ADA concentration).

The drug tolerance of the interference-suppressed drug-tolerant anti-drug antibody assay as reported herein with 1:1 conjugates of the monovalent bonded biotin and digoxygenin to the capture and tracer drug antibody, respectively, was evaluated by determining the highest TCZ concentration at which a given concentration of positive control ADA can be detected above the cut-point. Table 3 presents a summary of the results.

TABLE 3

Determination of drug (tocilizumab) tolerance in the interference-suppressed drug-tolerant anti-drug antibody ELISA with 1:1 conjugates of biotin and digoxygenin to the capture and tracer drug antibody as reported herein. Left-aligned signal values are below the plate-specific cut-point of 0.037 AU.

| ADA [ng/mL] | tocilizumab [µg/mL] | | | | | |
|---|---|---|---|---|---|---|
| | 80 | 70 | 60 | 50 | 5 | 0 |
| | signal mean [AU] | | | | | |
| 500 | 0.090 | 0.097 | 0.112 | 0.122 | 0.380 | 1.071 |
| 250 | 0.057 | 0.061 | 0.067 | 0.075 | 0.215 | 0.653 |
| 125 | 0.043 | 0.045 | 0.048 | 0.053 | 0.133 | 0.343 |
| 0.0 | 0.025 | 0.024 | 0.026 | 0.027 | 0.030 | 0.027 |

In the interference-suppressed drug-tolerant anti-drug antibody ELISA as reported herein an ADA concentration of 250 ng/mL was detected and tested positive in the presence of 80 µg/mL TCZ.

Interference Suppression:

Sixteen clinical serum samples were analyzed by a conventional anti-drug antibody assay as described in Stubenrauch et al. (supra). The results are summarized in Table 4a.

TABLE 4a

Results of the analysis of 16 serum samples from rheumatoid arthritis patients treated with tocilizumab with the ADA assay according to Stubenrauch et al. (supra).

| sample No. | conventional ADA assay |
|---|---|
| 1 | + |
| 2 | + |
| 3 | + |
| 4 | + |
| 5 | + |
| 6 | + |
| 7 | + |
| 8 | − |
| 9 | − |
| 10 | − |
| 11 | − |
| 12 | − |
| 13 | − |
| 14 | − |
| 15 | − |
| 16 | + |

Without alteration of the assay principle, a series of measures were taken to obtain an interference-suppressed drug tolerant anti-drug antibody ELISA as reported herein.

These are:
1) increasing the concentration of biotinylated and digoxigenylated TCZ (e.g. from 0.5 µg/mL to 1.5 µg/mL);
2) simultaneous incubation of the serum sample with TCZ-Bi and TCZ-Dig;
3) prolonged incubation of the serum sample with TCZ-Bi and TCZ-Dig (e.g. from 1 hour to 16 hours);

4) use of only lysine-coupled TCZ-Bi and TCZ-Dig reagents instead of a mixture of lysine- and carbohydrate-coupled reagents;
5) use of an increased serum matrix content; and
6) addition of oligomeric human IgG to the sample prior to incubation TCZ-Bi and TCZ-Dig.

The results as obtained with the interference suppressed assay as reported herein is shown in the following Table 4b.

TABLE 4b

Comparative analysis of 16 serum samples from rheumatoid arthritis patients treated with tocilizumab with the conventional and the herein reported interference suppressed ADA assay.

| sample No. | conventional ADA assay | interference suppressed ADA assay |
|---|---|---|
| 1 | + | + |
| 2 | + | + |
| 3 | + | + |
| 4 | + | + |
| 5 | + | + |
| 6 | + | + |
| 7 | + | + |
| 8 | − | − |
| 9 | − | − |
| 10 | − | − |
| 11 | − | − |
| 12 | − | − |
| 13 | − | − |
| 14 | − | − |
| 15 | − | + |
| 16 | + | − |

It has been found that if only a part of the measures as outlined above were taken the reduction of interference was not sufficient and still a susceptibility to interference by rheumatoid factors existed resulting in false-positive ADA assay results.

If, for example, only the measures
1) increasing the concentration of biotinylated and digoxigenylated TCZ (e.g. from 0.5 µg/mL to 1.5 µg/mL);
2) simultaneous incubation of the serum sample with TCZ-Bi and TCZ-Dig;
3) prolonged incubation of the serum sample with TCZ-Bi and TCZ-Dig (e.g. from 1 hour to 16 hours);
4) use of only lysine-coupled TCZ-Bi and TCZ-Dig reagents instead of a mixture of lysine- and carbohydrate-coupled reagents; and
5) use of an increased serum matrix content were taken not the full reduction of susceptibility to false positive assay results can be seen. The comparative data is shown in Table 4c.

TABLE 4c

Comparative analysis of 16 serum samples from rheumatoid arthritis patients treated with tocilizumab with the different formats of the ADA assay.

| sample No. | interference-suppressed ADA assay as reported herein | |
|---|---|---|
| | without additive | with additive |
| 1 | + | + |
| 2 | + | + |
| 3 | + | + |
| 4 | + | + |

TABLE 4c-continued

Comparative analysis of 16 serum samples from rheumatoid arthritis patients treated with tocilizumab with the different formats of the ADA assay.

| sample No. | interference-suppressed ADA assay as reported herein | |
|---|---|---|
| | without additive | with additive |
| 5 | + | + |
| 6 | + | + |
| 7 | + | + |
| 8 | + | − |
| 9 | − | − |
| 10 | + | − |
| 11 | + | − |
| 12 | + | − |
| 13 | + | − |
| 14 | + | − |
| 15 | + | + |
| 16 | + | − |

Comparative evaluation of 258 different serum samples from TCZ-treated RA patients with the conventional ADA assay and the interference-suppressed drug-tolerant ADA assay as reported herein showed the same positive results in 12 Samples. The conventional assay measured 27 placebo patients positive whereas the interference-suppressed drug-tolerant ADA assay as reported herein only 4. In conclusion, the set of measures as described herein and the addition of oligomeric human IgG as an ADA assay additive conferred increased drug tolerance and suppressed interference by RF compared to the conventional ADA assay.

A subset analysis of above-mentioned data is shown in Table 7 below.

TABLE 7

| Patient | conventional ELISA | | interference-suppressed ELISA | |
|---|---|---|---|---|
| P1 | + | 0.812 | + | 0.110 |
| P2 | + | 1.009 | + | 0.893 |
| P2 | − | 0.097 | + | 0.088 |
| P2 | + | 0.276 | + | 0.228 |
| P3 | + | 0.349 | + | 0.566 |
| P3 | + | 2.405 | + | 1.760 |
| P3 | + | 1.307 | + | 1.001 |
| P4 | + | 1.409 | + | 0.242 |
| P5 | + | 0.219 | + | 0.060 |
| P6 | + | 0.387 | + | 0.688 |
| P6 | + | 3.689 | + | 3.721 |
| P6 | + | 3.506 | + | 3.722 |
| P7 | + | 0.771 | + | 0.058 | study related CP: 0.215 (conventional ELISA); 0.058 (interference-suppressed ELISA); +: positive ELISA result; −: negative ELISA result In Table 8a assay signals for 27 placebo patients not treated with TCZ are shown. Due to the absence of TCZ-treatment induced ADA, high assay signals in this group are not expected and would indicate a potential interference.

TABLE 8a

| Patient | conventional ELISA | | interference-suppressed ELISA | |
|---|---|---|---|---|
| P8 | + | 0.270 | − | 0.032 |
| P8 | + | 0.231 | − | 0.033 |
| P9 | + | 3.736 | − | 0.055 |

TABLE 8a-continued

| Patient | conventional ELISA | | interference-suppressed ELISA | |
|---|---|---|---|---|
| P9  | + | 3.297 | + | 0.058 |
| P9  | + | 2.863 | − | 0.046 |
| P9  | + | 3.739 | − | 0.052 |
| P1  | + | 0.812 | + | 0.110 |
| P10 | + | 0.755 | − | 0.021 |
| P10 | + | 0.635 | − | 0.021 |
| P11 | + | 0.272 | − | 0.020 |
| P11 | + | 0.271 | − | 0.021 |
| P11 | + | 0.234 | − | 0.020 |
| P12 | + | 1.157 | − | 0.027 |
| P12 | + | 1.362 | − | 0.028 |
| P12 | + | 1.149 | − | 0.029 |
| P4  | + | 0.522 | − | 0.033 |
| P4  | + | 1.409 | + | 0.242 |
| P4  | + | 0.651 | − | 0.047 |
| P13 | + | 0.349 | − | 0.023 |
| P14 | + | 0.245 | − | 0.033 |
| P14 | + | 0.276 | − | 0.035 |
| P14 | + | 0.275 | − | 0.037 |
| P15 | + | 0.580 | − | 0.049 |
| P7  | + | 0.990 | − | 0.056 |
| P7  | + | 0.822 | − | 0.052 |
| P7  | + | 0.523 | − | 0.042 |
| P7  | + | 0.771 | + | 0.058 | study related cut-point (CP): 0.215 (conventional ELISA); 0.058 (interference-suppressed ELISA); +: positive ELISA result; −: negative ELISA result Signal pattern of both assay are very different: whereas all 27 placebos samples were determined to be positive using the conventional ELISA, but only 4 out of the 27 sample were determined to be positive with the interference-suppressed ELISA as reported herein.

In addition to placebo-treated patients sample of TCZ-treated patients have been analyzed. In Table 8b results for the patients prior to TCZ-treatment are shown. In Table 8c results for TCZ-treated patients are shown.

TABLE 8b

| Patient | Time point | conventional ELISA | | interference-suppressed ELISA | | dosing |
|---|---|---|---|---|---|---|
| P2  | baseline | + | 1.009 | + | 0.893 | 4 |
| P16 | baseline | + | 0.745 | − | 0.021 | 8 |
| P17 | baseline | + | 0.281 | − | 0.020 | 8 |
| P18 | baseline | + | 1.401 | − | 0.023 | 4 | study related CP: 0.215 (conventional ELISA); 0.058 (interference-suppressed ELISA); +: positive ELISA result; −: negative ELISA result TABLE 8c

| Patient | Time point | conventional ELISA | | interference-suppressed ELISA | | dosing |
|---|---|---|---|---|---|---|
| P19 | week 24 | + | 0.281 | − | 0.030 | 4 mg/kg |
| P19 | week 24 | + | 0.226 | − | 0.031 | 4 mg/kg |
| P19 | week 4  | + | 0.293 | − | 0.030 | 4 mg/kg |
| P19 | week 8  | + | 0.362 | − | 0.028 | 4 mg/kg |
| P2  | week 4  | − | 0.097 | + | 0.088 | 4 mg/kg |
| P2  | week 8  | + | 0.276 | + | 0.228 | 4 mg/kg |
| P16 | week 24 | + | 0.416 | − | 0.030 | 8 mg/kg |
| P16 | week 4  | + | 0.542 | − | 0.029 | 8 mg/kg |
| P16 | week4   | + | 0.397 | − | 0.024 | 8 mg/kg |
| P3  | week 24 | + | 2.405 | + | 1.760 | 4 mg/kg |
| P3  | week 28 | + | 1.307 | + | 1.001 | 4 mg/kg |
| P3  | week 4  | − | 0.181 | + | 0.120 | 4 mg/kg |
| P3  | week 8  | + | 0.349 | + | 0.566 | 4 mg/kg |
| P20 | week 8  | + | 0.818 | − | 0.034 | 4 mg/kg |
| P21 | week 4  | + | 0.289 | − | 0.031 | 8 mg/kg |

TABLE 8c-continued

| Patient | Time point | conventional ELISA | | interference-suppressed ELISA | | dosing |
|---|---|---|---|---|---|---|
| P17 | week 12 | + | 0.369 | − | 0.023 | 8 mg/kg |
| P17 | week 24 | + | 0.330 | − | 0.022 | 8 mg/kg |
| P17 | week 4  | + | 0.488 | − | 0.022 | 8 mg/kg |
| P17 | week 4  | + | 0.465 | − | 0.025 | 8 mg/kg |
| P17 | week 8  | + | 0.409 | − | 0.026 | 8 mg/kg |
| P18 | week 4  | + | 1.218 | − | 0.026 | 4 mg/kg |
| P18 | week 4  | + | 1.041 | − | 0.028 | 4 mg/kg |
| P5  | week 28 | + | 0.219 | + | 0.060 | 8 mg/kg |
| P6  | week 12 | + | 3.689 | + | 3.721 | 4 mg/kg |
| P6  | week 24 | + | 3.506 | + | 3.722 | 4 mg/kg |
| P6  | week 8  | + | 0.387 | + | 0.688 | 4 mg/kg |
| P22 | week24  | + | 0.423 | − | 0.020 | 4 mg/kg | study related CP: 0.215 (conventional ELISA); 0.058 (interference-suppressed ELISA); +: positive ELISA result; −: negative ELISA result The assay as reported herein provides a benefit independent from the therapeutic antibody and the target employed. This is shown in the following Table for an anti-IL6R antibody, an anti-IGF-1R antibody, an anti-IL13Ralpha antibody, an anti-OX40L antibody and an anti-Abeta antibody using samples of patients being diagnosed positive for rheumatoid arthritis.

TABLE 9a anti-IL6R antibody

| Patient | conventional ELISA | | interference-suppressed ELISA | |
|---|---|---|---|---|
| P23 | + | 0.169 | − | 0.079 |
| P24 | + | 0.197 | − | 0.082 |
| P25 | + | 0.240 | − | 0.110 |
| P26 | − | 0.131 | − | 0.088 |
| P27 | + | 0.215 | − | 0.111 |
| P28 | + | 0.199 | − | 0.136 |
| P29 | − | 0.135 | − | 0.085 |
| P30 | + | 0.220 | − | 0.086 |
| P31 | + | 0.158 | − | 0.100 |
| P32 | + | 0.221 | − | 0.132 |
| P33 | − | 0.110 | − | 0.081 |
| P34 | − | 0.099 | − | 0.090 |
| P35 | − | 0.100 | − | 0.082 |
| P36 | − | 0.098 | − | 0.076 |
| CP  |   | 0.157 |   | 0.140 |

TABLE 9b anti-IGF-1R antibody

| Patient | conventional ELISA | | interference-suppressed ELISA | |
|---|---|---|---|---|
| P23 | − | 0.153 | − | 0.127 |
| P24 | + | 0.423 | − | 0.132 |
| P25 | + | 0.266 | − | 0.145 |
| P26 | − | 0.171 | − | 0.163 |
| P27 | − | 0.152 | − | 0.132 |
| P28 | − | 0.133 | − | 0.120 |
| P29 | + | 0.245 | − | 0.124 |
| P30 | − | 0.173 | − | 0.142 |
| P31 | − | 0.152 | − | 0.115 |
| P32 | − | 0.172 | − | 0.131 |
| P33 | − | 0.131 | − | 0.134 |
| P34 | − | 0.124 | − | 0.115 |
| P35 | + | 0.189 | + | 0.189 |
| P36 | − | 0.157 | − | 0.154 |
| CP  |   | 0.176 |   | 0.185 |

TABLE 9c anti-IL13Ralpha antibody

| Patient | conventional ELISA | | interference-suppressed ELISA | |
|---|---|---|---|---|
| P23 | + | 0.556 | − | 0.080 |
| P24 | + | 0.881 | + | 0.198 |
| P25 | + | 2.192 | + | 0.761 |
| P26 | + | 0.674 | + | 0.235 |
| P27 | + | 0.604 | − | 0.044 |
| P28 | + | 0.177 | − | 0.000 |
| P29 | − | 0.000 | − | 0.006 |
| P30 | + | 0.424 | − | 0.091 |
| P31 | + | 0.342 | − | 0.000 |
| P32 | + | 0.353 | − | 0.092 |
| P33 | + | 0.208 | − | 0.021 |
| P34 | − | 0.000 | − | 0.000 |
| P35 | − | 0.079 | − | 0.097 |
| P36 | + | 0.238 | + | 0.235 |
| CP | | 0.100 | | 0.100 |

TABLE 9d anti-OX40L antibody

| Patient | conventional ELISA | | interference-suppressed ELISA | |
|---|---|---|---|---|
| P23 | + | 0.148 | − | 0.073 |
| P24 | + | 0.477 | − | 0.066 |
| P25 | + | 0.414 | + | 0.087 |
| P26 | − | 0.103 | − | 0.067 |
| P27 | + | 0.137 | − | 0.072 |
| P28 | + | 0.211 | + | 0.126 |
| P29 | − | 0.116 | − | 0.074 |
| P30 | + | 0.436 | − | 0.064 |
| P32 | + | 0.198 | − | 0.079 |
| P33 | + | 0.122 | − | 0.078 |
| P34 | − | 0.096 | − | 0.070 |
| P35 | − | 0.088 | − | 0.067 |
| P36 | + | 0.121 | − | 0.076 |
| CP | | 0.117 | | 0.085 |

TABLE 9e anti-Abeta antibody

| Patient | conventional ELISA | | interference-suppressed ELISA | |
|---|---|---|---|---|
| P25 | + | 0.063 | − | 0.025 |
| P26 | − | 0.025 | − | 0.026 |
| P28 | + | 0.086 | + | 0.080 |
| P29 | − | 0.020 | − | 0.021 |
| P30 | − | 0.037 | − | 0.022 |
| P31 | − | 0.036 | − | 0.024 |
| P32 | − | 0.029 | − | 0.024 |
| P33 | − | 0.027 | − | 0.026 |
| P34 | + | 0.069 | + | 0.069 |
| P35 | − | 0.019 | − | 0.021 |
| P36 | − | 0.033 | − | 0.032 |
| CP | | 0.044 | | 0.042 |

The following examples and figures are provided to aid the understanding of the present invention, the true scope of which is set forth in the appended claims. It is understood that modifications can be made in the procedures set forth without departing from the spirit of the invention.

EXAMPLES

Materials and Methods

Purified pooled human immunoglobulin class G (IgG) was prepared as described by Stubenrauch et al. (Anal. Biochem. 390 (2009) 189-196). Briefly, pooled human serum from healthy donors has been delipidated with Aerosil (silicon dioxide, 1.5% (w/v)) and precipitated with ammonium sulfate (ad 2.0 M). The pellet was homogenized in phosphate buffer and dialyzed against phosphate buffer, pH 7.0.

The mixture was separated by DEAE ion exchange chromatography at pH 7.0 and the IgG in the flow through was concentrated to 5.93 mg/mL and purified by gel filtration.

Polyclonal anti-digoxigenin-horse radish peroxidase (HRP) conjugate (Fab fragments) was obtained from Roche Diagnostics GmbH, Mannheim, Germany (cat. no. 11633716). Polyclonal rabbit anti-TCZ antibodies (0.5 mg-equivalent/mL) used as positive quality controls (QC) and calibration standards (CS) were prepared as described in Stubenrauch et al. (supra).

Individual human serum samples were provided by the serum bank of Roche Diagnostics GmbH, Penzberg, Germany. Pooled human serum matrix for negative control was supplied by TCS Biosciences Ltd., Buckingham, UK.

The following reagents were obtained from Roche Diagnostics GmbH, Mannheim, Germany: 2,2'-azino-bis(3-ethylbenzthiazoline-6-sulfonic acid (ABTS) substrate (cat. no. 11684302-001), the washing buffer for the ELISA: phosphate-buffered saline (PBS) (0.01 M KH2PO4, 0.1 M Na2HPO4, 1.37 M NaCl, 0.027 M KCl; pH 7.0)/0.05% polysorbate 20 (Tween 20) (cat. no. 11332465-001) and the ready-to-use Universal buffer (cat no. 4742672) which was used as dilution buffer in the ELISA. All chemicals were of analytical grade.

Streptavidin-coated microtiter plates (SA-MTP) were obtained from MicroCoat Biotechnologie GmbH, Bernried. Uncoated Nunc 96-microwell plates were from Fisher Scientific GmbH, Schwerte, Germany (cat no. 442587) and used for pre-incubation.

Conventional Anti-Drug Antibody Assay:

The assay was performed at room temperature. In the first step, TCZ-Bi was bound to SA-MTPs at a concentration of 0.5 µg/ml by incubating 100 µL on a shaker at 400 rpm for 1 hour. Before adding the pre-incubation solution to the SA-MTPs, the excess unbound TCZ-Bi was removed by washing 3 times. In parallel with the coating procedure, pre-incubation of standards and samples was performed in duplicate in a separate uncoated 96-well plate. The samples and standards were diluted (1:10) in the wells with 10% serum matrix to a volume of 75 µL and mixed with the same volume of TCZ-DIG, starting the one hour pre-incubation period. The TCZ-Bi-coated SA-MTPs were loaded with the pre-incubation solutions by transferring 100 µL from each well of the pre-incubation plate to the wells of the coated MTP and incubated on a shaker at 400 rpm for one hour. After washing, polyclonal anti-Dig horseradish peroxidase (HRP) conjugate in a volume of 100 µL (100 mU/mL) was added to the wells and incubated on a shaker for one hour. After washing, the HRP-catalyzed color-generating reaction was initiated by adding 100 µL ABTS solution. When the maximum optical density (OD) was about 2.0, usually within 20 to 30 minutes, the signal of the color reaction was measured by an ELISA reader at a wave length of 405 nm (reference, 490 nm). The same assay was performed in the presence of the confirmation reagents, with simultaneous measurement without the confirmation reagents. The obtained OD data were used for generating the standard calibration curve by nonlinear 4-parameter regression curve fitting according to the Wiemer-Rodbard method for calculating the sample concentration.

The cutoff points for the test results were set at the 95% CIs of the assay signals (OD) from multiple analyses of human blank serum samples from healthy volunteers and patients with RA. A screening test result was considered positive at a value above the cutoff. A decrease in absorbance of >20% relative to the non-spiked sample indicated a positive result. The screening cutoff was determined at 61.4 ng/mL of reference antibody. Intra-assay and inter-assay accuracy were 84.8% to 93.1% and 91.3% to 92.2%, respectively. The corresponding values for intra-assay and inter-assay precision were 1.8% to 2.0% and 6.8% to 8.0%. The accuracy of the ELISA was defined by the extent to which the results of the assay agreed with the true values. Accuracy was determined by comparing measured concentrations of the rabbit polyclonal anti-TCZ-positive control standard spiked into human serum with nominal concentrations of anti-TCZ. High-concentration (360 ng equivalents/mL) and low-concentration (60 ng equivalents/mL) positive control standards were analyzed in six aliquots of each positive control standard measured in duplicate to determine intra-assay accuracy and in three aliquots of each positive control standard measured in duplicate to determine inter-assay accuracy.

Example 1

Biotinylation of Anti-IL6R Antibody Tocilizumab a) Preparation of Conventionally Biotinylated IgG The anti-IL6R antibody tocilizumab has been dialyzed against buffer (100 mM potassium phosphate buffer (in the following denoted as K-PO4), pH 8.5). Afterwards the solution was adjusted to a protein concentration of 5 mg/ml. D-biotinoyl-aminocaproic acid-N-hydroxysuccinimide ester was dissolved in dimethyl sulphoxide (DMSO) and added to the antibody solution in a molar ratio of 1:5. After 60 minutes the reaction was stopped by adding L-lysine. The surplus of the labeling reagent was removed by dialysis against 50 mM K-PO4 supplemented with 150 mM KCl, pH 7.5. Aliquots of TCZ-Bi were stored including 6.5% sucrose at −80° C.

b) Preparation of Mono Biotinylated IgG

The anti-IL6R antibody tocilizumab has been dialyzed against 100 mM K-PO4, pH 8.5 and afterwards the solution was adjusted to a protein concentration of 5 mg/ml. D-biotinoyl-aminocaproic acid-N-hydroxysuccinimide ester was dissolved in dimethyl sulphoxide (DMSO) and added to the antibody solution in a molar ratio of 1:1. After 60 minutes the reaction was stopped by adding L-lysine. The surplus of the labeling reagent was removed by dialysis against 25 mM K-PO4 supplemented with 150 mM KCl, pH 7.2. The mixture was transferred to a buffer with 100 mM K-PO4, 150 mM KCl, pH 7.2 including 1 M ammonium sulfate and applied to a column with streptavidin mutein sepharose. The non biotinylated IgG is in the flow through, the mono biotinylated IgG is eluted with 100 mM K-PO4, 150 mM KCl, 1.5% DMSO, pH 7.2 and the biotinylated IgG including higher biotinylated populations is eluted with 100 mM K-PO4, 150 mM KCl, 2 mM D-biotin, pH 7.2. The mono biotinylated antibody was dialyzed against 50 mM K-PO4 supplemented with 150 mM KCl, pH 7.5. The aliquots were stored including 6.5% sucrose at −80° C.

Example 2

Digoxigenylation of Anti-IL6R Antibody Tocilizumab a) Preparation of Conventionally Digoxigenylated IgG The anti-IL6R antibody tocilizumab has been dialyzed against buffer (100 mM potassium phosphate buffer (in the following denoted as K-PO4), pH 8.5). Afterwards the solution was adjusted to a protein concentration of 5 mg/ml. Digoxigenin 3-O-methylcarbonyl-ε-aminocaproic acid-N-hydroxysuccinimide ester was dissolved in DMSO and added to the antibody solution in a molar ratio of 1:4. After 60 minutes the reaction has been stopped by adding L-lysine. The surplus of labeling reagent was removed by dialysis against 50 mM K-PO4 supplemented with 150 mM NaCl, pH 7.5. Digoxigenylated TCZ (TCZ-Dig) was stored in aliquots including 6.5% sucrose at −80° C.

b) Preparation of Mono Digoxigenylated IgG

The anti-IL6R antibody tocilizumab has been dialyzed against 100 mM K-PO4, pH 8.5 and afterwards the solution was adjusted to a protein concentration of 5 mg/ml. Digoxigenin 3-O-methylcarbonyl-ε-aminocaproic acid-N-hydroxysuccinimide ester was dissolved in dimethyl sulphoxide (DMSO) and added to the antibody solution in a molar ratio of 1:1. After 60 minutes the reaction was stopped by adding L-lysine. The surplus of the labeling reagent was removed by dialysis against 50 mM K-PO4 supplemented with 150 mM KCl, pH 7.5. The mixture was applied to a sepharose column with immobilized monoclonal antibodies against digoxigenin. The non digoxigenylated antibody is in the flow through, the mono digoxigenylated IgG is eluted with gentle elution buffer (Thermo Scientific, #21013) and the digoxigenylated antibody including higher digoxigenylated populations is eluted with 1 M propionic acid. The fraction with mono digoxigenylated antibody was dialyzed first against 20 mM TRIS, 20 mM NaCl, pH 7.5 and second against 50 mM K-PO4, 150 mM KCl, pH 7.5. The aliquots were stored including 6.5% sucrose at −80° C.

Example 3

Generation of Human IgG in Oligomeric Form

Human IgG purified from human serum by ion exchange chromatography was dialyzed against 150 mM potassium phosphate buffer containing 100 mM NaCl, pH 8.4, and the protein solution was concentrated to a protein concentration of 50 mg/ml. Disuccinimidyl suberate (DSS) was dissolved in DMSO and added to the antibody solution in a molar ration of 1:6 (IgG:DSS). The mixture was incubated at 25° C. and pH 8.4 with stirring and the reaction was analyzed with an analytical gel filtration column (e.g. using a TSK 4000 column). The polymerization was stopped after 140 min. by adding lysine to a final concentration of 20 mM. After 45 min. incubation at 25° C. the oligomeric human IgG was separated by gel filtration (e.g. using a Sephacryl 5400 column) to remove low molecular fractions. The composition of the oligomers was characterized by UV spectroscopy, size exclusion chromatography and SDS-PAGE gel electrophoresis. The oligomeric human IgG was aliquoted (10.5 mg/mL) and stored at −65° C. until it was freshly diluted with Universal buffer (cat no. 4742672) to a concentration of 55.6 μg/mL for use as ADA assay additive (AAA) in the immunoassay.

Example 4

Preparation of Calibration Standards and Quality Control Samples

Stock solutions for calibration standards (CS) and quality control samples (QC) were prepared separately. The CS samples were freshly prepared at the assay day using a 0.5 mg/mL stock solution of TCZ. After pre-dilution with human pooled serum (HPS), the resulting CS working solution was stepwise 1:1 diluted with 100% HPS to yield calibrator concentrations of 1,000; 500; 250; 125; 62.5; 31.3; and 15.6 ng/mL before use in the assay. The negative control was 100% HPS. For the pre-incubation step in the assay, the CS samples were diluted 1:10 to adjust to a serum concentration of 10% and an assay concentration range of 100 ng/mL to 1.56 ng/mL.

The QC stock samples used were made in 100% human pooled serum and stored as single use aliquots at −20° C. Three separate QC samples were prepared and stored at stock concentrations representing high (750 ng/mL), medium (400 ng/mL) and low (50 ng/mL) undiluted serum concentrations. For the pre-incubation step in the assay the QC samples were freshly diluted 1:10 in the capture/detection solution to reach a serum concentration of 10%. A fourth QC sample at the typical cut point of the assay at 25 ng/mL was further used.

Example 5

ADA Screening and Confirmation Assay

A sandwich ELISA was used for both screening and confirmation of anti-drug antibodies (ADAs) against tocilizumab (TCZ) (see Stubenrauch, K., et al., Clin. Ther. 32 (2010) 1597-1609). The principle of the method is the capture of ADAs in complex with TCZ-Dig and TCZ-Bi, the latter one leading to immobilization onto a streptavidin-coated plate. The TCZ-Bi/ADA/TCZ-Dig complex bound to the SA-MTP was detected by an anti-Dig-HRP enzyme conjugated antibody. The principle of the drug-tolerant anti-drug antibody assay is shown in FIG. 1. Inclusion of oligomeric IgG as ADA assay additive leads to an interference-suppressed anti-drug antibody assay as shown in FIG. 2. The horseradish peroxidase (HRP) of the polyclonal antibody catalyzes a color reaction of the substrate ABTS. The color intensity is proportional to the concentration of the analyte.

The screening assay was performed at room temperature. Reagents and serum samples were diluted with Universal buffer (cat no. 4742672), all washing steps were performed with the washing buffer (PBS, 0.05% polysorbate 20 (Tween 20) (cat. no. 11332465-001)) three times with 300 μL per well. Incubations were performed under shaking on a microtiter plate shaker (MTP shaker) at 500 rpm. Test samples, QC and CS samples were incubated overnight (up to 16 hours) with the capture antibody TCZ-Bi and the detection antibody TCZ-Dig. Each well of the pre-incubation microtiter plate (MTP) was loaded with 225 μL of the capture/detection solution containing 1.667 μg/mL TCZ-Bi and 1.667 μg/mL TCZ-Dig with oligomeric human IgG ADA assay additive (AAA) and thereafter 25 μL of the respective samples were added. The resulting concentrations of TCZ-Bi and TCZ-Dig were 1.5 μg/mL each and the oligomeric human IgG had a concentration of 50 μg/mL. The loaded MTP was covered to prevent evaporation and incubated overnight. Duplicates of 100 μL of each well of the pre-incubation plate were transferred to the wells of a streptavidin-coated microtiter plate (SA-MTP) which was covered and incubated for 1 h.

After washing, the polyclonal anti-Dig Fab-HRP conjugate with a concentration of 25 mU/mL was added in a volume of 100 μL to each well and incubated for 1 h. After washing, the ABTS ready-to-use solution was added in 100 μL aliquots to each well and incubated for about 10 to 15 min. while shaking. The signal of the color-generating reaction was measured by an ELISA reader at 405 nm wavelength (reference wavelength: 490 nm). Absorbance values of each serum sample were determined in triplicates. The highest standard should reach an optical density (OD) between 1.8 and 2.2 arbitrary units (AU). The obtained OD data was used for generating the standard calibration curve by non-linear 4-paramter fit "Wiemer Rodbard" for calculating the sample concentration. A sample was confirmed as positive to ADAs if the recovery of the concentration was less than the specificity cut-point.

Evaluation of the specificity cut-point was performed by analysis of 32 individual blank human serum samples of rheumatoid arthritis patients in duplicates on one MTP. The cut-point specifies the signal above which a sample is defined as potentially positive for the presence of ADAs in the ADA screening assay. Due to non-normality of the data, a non-parametric approach with a 95% percentile was applied for cut-point calculation based on the mean of cut-points on replicate plates.

The experiments conducted to determine the cut-point of the ADA assay from duplicate measurements of 32 individual human blank serum samples of rheumatoid arthritis patients revealed a mean AU of about 0.026 on three different plates with a standard deviation (SD) of about 0.009. The corresponding coefficient of variation (CV) was 23.8%; 20.0%; and 19.0%, respectively. Based on these data sets, a normalization factor of NF=1.6905 was derived which was used throughout the assay qualification and applied to plate-specific cut-points (plate specific cut-point [AU]=Signal [AU](negative control)×NF).

For qualification of the screening ADA assay, five independent calibration curve preparations with seven calibrator samples with an assay concentration range of 1.56 ng/mL to 100 ng/mL and a blank sample were measured in duplicates on one plate. The intra-assay qualification runs were performed with five replicates (five separate vials) with each of the four QC samples measured in duplicates on a single plate. Inter-assay qualification data for all QC samples measured in duplicates were obtained from seven independent test runs performed by at least two operators on four different days.

Figure 3:
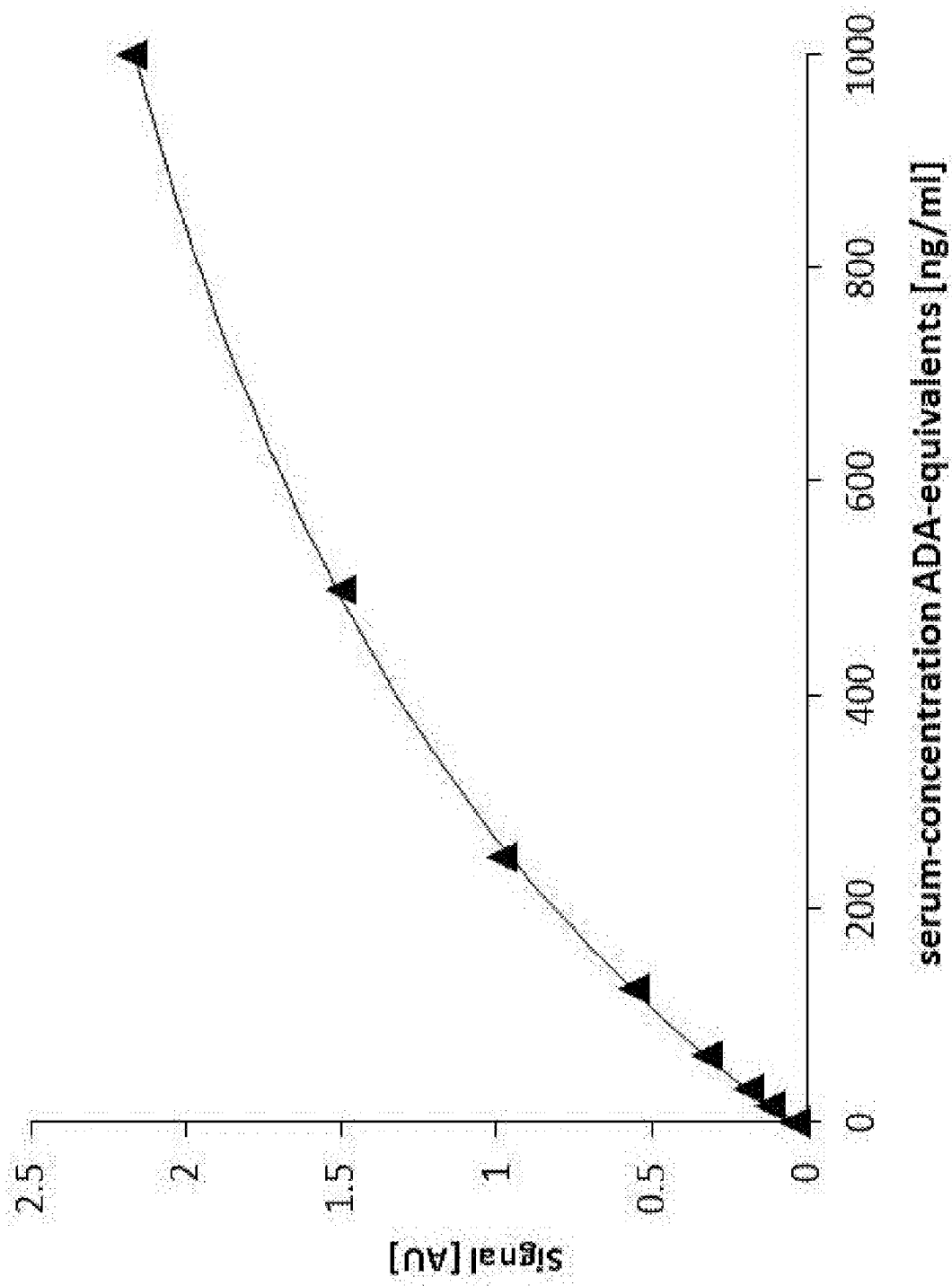
FIG. 3 Calibration curve obtained for the interference-suppressed anti-drug antibody assay for anti-IL6R antibody tocilizumab.

A typical calibration curve of the interference-suppressed ELISA is shown in FIG. 3. The precision of duplicate measurements of samples was assessed during the qualification experiments and its CV did not exceed 15%. Intra-assay and inter-assay precision and accuracy values of the interference-suppressed ADA ELISA are summarized in Table 5.

TABLE 5

Determination of intra-assay and inter-assay precision and accuracy of the interference-suppressed ELISA using tocilizumab-specific ADAs spiked into human serum.

| | ADA concentration in 100% serum [ng/mL] | | | | | |
|---|---|---|---|---|---|---|
| | Intra-assay (n = 5) | | | Inter-assay (n = 7) | | |
| | High QC | Mid QC | Low QC | High QC | Mid QC | Low QC |
| spiked (expected concentration) | 750 | 400 | 50 | 750 | 400 | 50 |
| mean of measured concentration | 683 | 382 | 50.8 | 696 | 402 | 52.5 |
| SD of measured concentration | 15.6 | 15.8 | 1.33 | 21.2 | 13.6 | 2.8 |
| precision (% CV) | 2.28 | 4.14 | 2.62 | 3.04 | 3.38 | 5.33 |
| accuracy (% recovery) | 91.1 | 95.5 | 102 | 92.8 | 101 | 105 |

The determined intra-assay precision was <5% for all QCs including the cut-point QC of 25 ng/mL. The determined intra-assay accuracy was in the range of 91.1% to 102% and all cut-point QC samples tested positive. The inter-assay precision for back-calculated QCs was <6% for all QCs. The determined inter-assay accuracy was 92.8% to 105% for the high, medium and low QCs. All cut-point QC measurements provided ADA-positivity.

A potential high-dose hook effect was assessed by serial titration (1:2) of a positive control sample within an assay concentration range of 25,000 ng/mL to 6.1 ng/mL. Recovery of ADA concentrations within the assay range was between 77.9% and 98.9%. For analysis of potential matrix effects, 11 individual normal human serum samples were spiked at high and low dose QC, i.e. 50 and 750 ng/mL in 100% serum, with positive control ADA and were quantified. In addition, QC samples were also analyzed on the same plate. Recovery of the low and high ADA concentrations was 111% (range: 104 to 117%) and 111% (range: 107 to 117%), indicating that there was no matrix effect in the interference-suppressed ADA ELISA.

The drug tolerance was evaluated by determining the highest TCZ concentration at which a given concentration of positive control ADA can be detected above the cut-point. Table 2 presents a summary of a complete data set.

TABLE 2

Determination of drug (tocilizumab) tolerance in the interference-suppressed drug-tolerant anti-drug antibody ELISA as reported herein. Left-aligned signal values are above the plate-specific cut-point of 0.045 AU, right-aligned values are below the cut-point.

| ADA [ng/mL] | TCZ [μg/mL] | | | | | |
|---|---|---|---|---|---|---|
| | 100 | 30 | 10 | 3 | 1 | 0 |
| | signal mean [AU] | | | | | |
| 10,000 | 0.948 | 2.263 | 3.266 | 3.536 | 3.146 | 3.272 |
| 3,000 | 0.310 | 0.943 | 1.956 | >3.5 | 2.860 | 3.161 |
| 1,000 | 0.119 | 0.364 | 0.789 | 1.051 | 1.180 | 2.292 |
| 300 | 0.055 | 0.133 | 0.280 | 0.376 | 0.426 | 0.857 |
| 100 | 0.033 | 0.057 | 0.105 | 0.144 | 0.163 | 0.310 |
| 30 | 0.027 | 0.036 | 0.051 | 0.063 | 0.068 | 0.113 |
| 10 | 0.022 | 0.025 | 0.032 | 0.039 | 0.040 | 0.056 |
| 0 | 0.024 | 0.023 | 0.026 | 0.027 | 0.027 | 0.027 |

Concentrations of the anti-IL6R antibody tocilizumab to be detected in clinical samples are 0.5 μg/mL or higher, often in the range of from 1 μg/mL to 10 μg/mL. A very low ADA concentration of 30 ng/mL was detected and tested positive in the presence of 10 μg/mL TCZ. Furthermore ADA concentrations of 100 ng/mL and 300 ng/mL show a drug antibody tolerance of 30 μg/ml and even 100 μg/mL, respectively. The same experiments conducted with the previously used, two-step conventional ADA ELISA for tocilizumab revealed an at least 10-fold higher drug tolerance with the interference-suppressed assay (see FIG. 4 for 300 ng/mL ADA concentration).

The concentration of TCZ to be used as the excess free drug in the confirmation assay was based on the data set obtained in the drug interference experiments. To evaluate the TCZ concentration that can inhibit high levels of ADAs in the sample, four different concentrations of positive control samples (1,000; 500; 250; 83.3 ng/mL in 100% serum) were each incubated with increasing concentrations of TCZ (0; 16; 31; 63; 125; 250 μg/mL in 100% serum). The TCZ concentration that inhibited at least 95% (corresponding to less than 5% signal recovery) of the measured signal at high concentrations of the positive control ADA was determined to be 25 μg/mL of TCZ.

To reduce the likelihood of false-negatives due to affinity differences of ADAs in study samples during the later in-study testing phase, a two-fold higher excess free drug concentration of the determined value was used for further evaluation, i.e. 40 μg/mL assay concentration corresponding to 400 μg/mL in 100% serum.

The minimal signal inhibition value needed for confirming specific ADAs was determined by pre-incubation of 16 individual blank human serum samples of rheumatoid arthritis patients with TCZ and analyzed in duplicates in one test run. The analysis was performed with and without 400 μg/mL of free TCZ. It has been found that addition of free TCZ reduced the assay signal by a mean of 14.1% ranging from −11.5% to 34.8%, and a SD of 11.2%. Applying a 99.9% confidence interval (mean+3.09 SD) resulted in a minimal signal reduction of 49% for blank serum samples. Based on this calculation, a sample was assessed confirmation positive if the signal decreased by more than 49% in presence of excess free drug when compared with that in absence of free drug. As reference samples, the corresponding samples without excess TCZ were used. To demonstrate the reproducibility of signal inhibition in the confirmation assay, serum samples with high, medium and low positive QC concentrations were analyzed three times with and without excess TCZ at the predefined concentration.

The interference-suppressed ADA assay for TCZ had a measurement range of from 1,000 ng/mL to 15.6 ng/mL of ADA calibrator in 100% serum. Intra-assay precision was less than 5% for all quality controls and the intra-assay accuracy was 91.1% to 102%. The inter-assay precision and accuracy were less than 6% and 92.8% to 105%, respectively.

Qualification of the assay did exclude a hook and matrix effect.

It can be seen that the drug tolerance of the interference-suppressed ADA assay was at least 10-fold higher than that of the previous version.

The confirmation assay was performed essentially as described before for the screening assay except that samples were analyzed in parallel without and with excess free drug, i.e. TCZ. The confirmation capture/detection solution contained the same volume of the capture/detection solution with additional excess TCZ (44.4 μg/mL) to achieve a final assay concentration of 40 μg/mL TCZ after addition of the samples. Calculation of the percent signal inhibition under confirmatory conditions with excess drug was done using the following equation:

% signal inhibition=100×(1−([AU]drug-pretreated sample/[AU]untreated sample)).

Example 6

Application of the Interference-Suppressed ADA Assay to Clinical Samples

Measures to increase drug tolerance consisting in 1) increasing the concentration of biotinylated and digoxigenylated TCZ (e.g. to 1.5 μg/mL); 2) simultaneous incubation of the serum sample with TCZ-Bi and TCZ-Dig; 3) prolonged incubation of the serum sample with TCZ-Bi and TCZ-Dig (e.g. overnight); 4) use of only lysine-coupled TCZ-Bi and TCZ-Dig reagents instead of a mixture of lysine- and carbohydrate-coupled reagents; and use of an increased serum matrix (e.g. 10% instead of 5%) resulted in an increase of ADA positives from 12/28 to 25/28.

Sixteen clinical serum samples were analyzed by a set of three different ADA assays: the conventional ADA assay, interference-suppressed ADA assay as reported herein without added oligomeric human IgG, and the interference-suppressed ADA assay as reported herein with the addition of oligomeric human IgG. The results are summarized in Table 6. Of the 16 samples, 15 were tested positive in the version of the ADA assay wherein only measures 1 to 5 have been taken whereas only 8/16 tested positive in the conventional as well as in the interference-suppressed drug-tolerant ADA assay as reported herein wherein measures 1 to 6 have been taken, with identical results in seven of the eight samples. These seven samples with identical results were characterized by low RF concentrations in the samples and/or at baseline. All seven samples contained ADAs of the IgG isotype which bound to the Fab part of tocilizumab indicative of true tocilizumab specific ADAs. Three of the seven samples also had IgM isotype ADAs, but which also bound to the Fab part. In contrast, the vast majority of the remaining samples had ADAs predominantly of the IgM isotype which bound to the constant Fc part of tocilizumab. These samples also contained a high, i.e. >1,000 U/mL, concentration of RF.

TABLE 6

Comparative analysis of 16 serum samples from rheumatoid arthritis patients treated with tocilizumab with the different formats of the ADA assay, in the BIAcore assay and in the rheumatoid factor assay.

| | interference-suppressed ADA assay as reported herein | | con-ven-tional | BIAcore: isotype/epitope binding of | | RF assay [U/ml] | |
|---|---|---|---|---|---|---|---|
| sample No. | without additive | with additive | ADA assay | IgG ADA | IgM ADA | study sample | baseline |
| 1 | + | + | + | IgG/Fab | IgG | — | 312 |
| 2 | + | + | + | IgG/Fab | — | 324 | 324 |
| 3 | + | + | + | IgG/Fab | — | 591 | 324 |
| 4 | + | + | + | IgG/Fab | — | 56 | 37 |
| 5 | + | + | + | IgG/Fab | IgG/Fab | 117 | 129 |
| 6 | + | + | + | IgG/Fab | IgG/Fab | — | 47 |
| 7 | + | + | + | IgG/Fab | — | — | <15 |
| 8 | + | − | − | IgG/Fc | IgG/Fc | 2,870 | 1,305 |
| 9 | − | − | − | IgG/Fc | IgG/Fc | 1,790 | 1,790 |
| 10 | + | − | − | IgG/Fc | IgG/Fc | 1,630 | — |
| 11 | + | − | − | — | IgG/Fc | 2,320 | 1,393 |
| 12 | + | − | − | — | IgG/Fc | — | 5,510 |
| 13 | + | − | − | IgG/Fc | IgG/Fc | 1,500 | 1,315 |
| 14 | + | − | − | — | IgG/Fc; Fab | — | 107 |
| 15 | + | + | − | IgG/Fab; Fc | IgG/Fc | 4,450 | 2,620 |
| 16 | + | − | + | IgG | — | — | 1,099 |

The ADA immunoassay as reported in Example 5 was used to analyze 148 different serum samples from rheumatoid arthritis patients taken at baseline and after administration of tocilizumab. The results of the analysis with the interference-suppressed ADA assay were compared with those obtained by analysis with the conventional ADA immunoassay. For more detailed analysis, a total of 92 serum samples (out of the 148) from 18 different patients with additional information on ADA isotype and binding region as well as on clinical events were selected. Patients were selected if they fulfilled at least one of the following criteria: 1) ADA positive immune response at any time point; 2) high TCZ serum concentration; 3) clinical reaction such as infusion-related, hypersensitivity or anaphylaxis. Analysis of the binding region and the isotype of the ADAs were performed with a biosensor immunoassay as previously described (Stubenrauch, K., et al., Anal. Biochem. 390 (2009) 189-196). Briefly, the surface plasmon resonance (SPR) assay set up made use of the four parallel flow cells on a single biosensor chip by immobilization of full-length antibody and its constant (Fc) and antigen binding (Fab) fragments for differential binding analysis of ADAs. The positive control standard conjugates mimicking polyclonal human ADAs of different isotypes were obtained by conjugating polyclonal rabbit antibodies against TCZ to human immunoglobulin (Ig) M, IgG, or IgE (see WO 2008/061684). The Rheumatoid Factor (RF) assay was performed on the Siemens BN II Nephelometer using RF reagents from Siemens Healthcare Diagnostics (Newark, Del., USA). Briefly, polystyrene particles coated with an immune-complex consisting of human immunoglobulin and anti-human IgG from sheep are aggregated when mixed with samples containing RF. These aggregates scatter a beam of light passed through the sample. The intensity of the scattered light is proportional to the concentration of the respective protein in the sample. The result is evaluated by comparison with a standard of known concentration.

Comparative evaluation of 258 different serum samples from TCZ-treated RA patients with the conventional and interference-suppressed drug-tolerant ADA assay as reported herein showed the same positive results in 12 Samples. The conventional assay measured 27 placebo patients positive whereas the interference-suppressed drug-tolerant ADA assay as reported herein 4. In conclusion, the set of measures as described herein and the addition of oligomeric human IgG as an ADA assay additive conferred increased drug tolerance and suppressed interference by RF compared to the conventional ADA assay.

A subset analysis of above-mentioned data is shown in Table 7 below.

TABLE 7

| Patient | Time point | conventional ELISA | | interference-suppressed ELISA | | dosing |
|---|---|---|---|---|---|---|
| P1 | week 4 | + | 0.812 | + | 0.110 | placebo |
| P2 | baseline | + | 1.009 | + | 0.893 | 4 mg/kg |
| P2 | week 4 | − | 0.097 | + | 0.088 | 4 mg/kg |
| P2 | week 9 | + | 0.276 | + | 0.228 | 4 mg/kg |
| P3 | week 8 | + | 0.349 | + | 0.566 | 4 mg/kg |
| P3 | week 24 | + | 2.405 | + | 1.760 | 4 mg/kg |
| P3 | week 28 | + | 1.307 | + | 1.001 | 4 mg/kg |
| P4 | week 4 | + | 1.409 | + | 0.242 | 4 mg/kg |
| P5 | week 28 | + | 0.219 | + | 0.060 | 8 mg/kg |
| P6 | week 8 | + | 0.387 | + | 0.688 | 4 mg/kg |
| P6 | week 12 | + | 3.689 | + | 3.721 | 4 mg/kg |
| P6 | week 24 | + | 3.506 | + | 3.722 | 4 mg/kg |
| P7 | week 4 | + | 0.771 | + | 0.058 | placebo | study related CP: 0.215 (conventional ELISA); 0.058 (interference-suppressed ELISA); +: positive ELISA result; −: negative ELISA result In Table 8a assay signals for 27 placebo patients not treated with TCZ are shown as bars and numbers. Due to the absence of TCZ-treatment induced ADA, high assay signals in this group are not expected and would indicate a potential interference.

TABLE 8a

| Patient | Time point | conventional ELISA | | interference-suppressed ELISA | | dosing |
|---|---|---|---|---|---|---|
| P8 | baseline | + | 0.270 | − | 0.032 | placebo |
| P8 | week 4 | + | 0.231 | − | 0.033 | placebo |
| P9 | week8 | + | 3.736 | − | 0.055 | placebo |
| P9 | baseline | + | 3.297 | + | 0.058 | placebo |
| P9 | week 12 | + | 2.863 | − | 0.046 | placebo |
| P9 | week 4 | + | 3.739 | − | 0.052 | placebo |
| P1 | week 4 | + | 0.812 | + | 0.110 | placebo |
| P10 | week 4 | + | 0.755 | − | 0.021 | placebo |
| P10 | week 4 | + | 0.635 | − | 0.021 | placebo |
| P11 | baseline | + | 0.272 | − | 0.020 | placebo |
| P11 | week 4 | + | 0.271 | − | 0.021 | placebo |
| P11 | week 4 | + | 0.234 | − | 0.020 | placebo |
| P12 | baseline | + | 1.157 | − | 0.027 | placebo |
| P12 | baseline | + | 1.362 | − | 0.028 | placebo |
| P12 | week 4 | + | 1.149 | − | 0.029 | placebo |
| P4 | baseline | + | 0.522 | − | 0.033 | placebo |
| P4 | week 4 | + | 1.409 | + | 0.242 | placebo |
| P4 | week 4 | + | 0.651 | − | 0.047 | placebo |
| P13 | week 36 | + | 0.349 | − | 0.023 | placebo |
| P14 | week 4 | + | 0.245 | − | 0.033 | placebo |
| P14 | baseline | + | 0.276 | − | 0.035 | placebo |
| P14 | week 4 | + | 0.275 | − | 0.037 | placebo |
| P15 | week 4 | + | 0.580 | − | 0.049 | placebo |
| P7 | baseline | + | 0.990 | − | 0.056 | placebo |
| P7 | week 4 | + | 0.822 | − | 0.052 | placebo |

TABLE 8a-continued

| Patient | Time point | conventional ELISA | | interference-suppressed ELISA | | dosing |
|---|---|---|---|---|---|---|
| P7 | week 4 | + | 0.523 | − | 0.042 | placebo |
| P7 | week 4 | + | 0.771 | + | 0.058 | placebo | study related CP: 0.215 (conventional ELISA); 0.058 (interference-suppressed ELISA); +: positive ELISA result; −: negative ELISA result Signal pattern of both assay are very different: whereas all 27 placebos samples were determined to be positive using the conventional ELISA, only 4 out of the 27 sample were determined to be positive with the interference-suppressed ELISA as reported herein.

In addition to placebo-treated patients sample of TCZ-treated patients have been analyzed. In Table 8b results for the patients prior to TCZ-treatment are shown. In Table 8c results for TCZ-treated patients are shown.

TABLE 8b

| Patient | Time point | conventional ELISA | | interference-suppressed ELISA | | dosing |
|---|---|---|---|---|---|---|
| P2 | baseline | + | 1.009 | + | 0.893 | 4 |
| P16 | baseline | + | 0.745 | − | 0.021 | 8 |
| P17 | baseline | + | 0.281 | − | 0.020 | 8 |
| P18 | baseline | + | 1.401 | − | 0.023 | 4 | study related CP: 0.215 (conventional ELISA); 0.058 (interference-suppressed ELISA); +: positive ELISA result; −: negative ELISA result TABLE 8c

| Patient | Time point | conventional ELISA | | interference-suppressed ELISA | | dosing |
|---|---|---|---|---|---|---|
| P19 | week 24 | + | 0.281 | − | 0.030 | 4 mg/kg |
| P19 | week 24 | + | 0.226 | − | 0.031 | 4 mg/kg |
| P19 | week 4 | + | 0.293 | − | 0.030 | 4 mg/kg |
| P19 | week 8 | + | 0.362 | − | 0.028 | 4 mg/kg |
| P2 | week 4 | − | 0.097 | + | 0.088 | 4 mg/kg |
| P2 | week 8 | + | 0.276 | + | 0.228 | 4 mg/kg |
| P16 | week 24 | + | 0.416 | − | 0.030 | 8 mg/kg |
| P16 | week 4 | + | 0.542 | − | 0.029 | 8 mg/kg |
| P16 | week4 | + | 0.397 | − | 0.024 | 8 mg/kg |
| P3 | week 24 | + | 2.405 | + | 1.760 | 4 mg/kg |
| P3 | week 28 | + | 1.307 | + | 1.001 | 4 mg/kg |
| P3 | week 4 | − | 0.181 | + | 0.120 | 4 mg/kg |
| P3 | week 8 | + | 0.349 | + | 0.566 | 4 mg/kg |
| P20 | week 8 | + | 0.818 | − | 0.034 | 4 mg/kg |
| P21 | week 4 | + | 0.289 | − | 0.031 | 8 mg/kg |
| P17 | week 12 | + | 0.369 | − | 0.023 | 8 mg/kg |
| P17 | week 24 | + | 0.330 | − | 0.022 | 8 mg/kg |
| P17 | week 4 | + | 0.488 | − | 0.022 | 8 mg/kg |
| P17 | week 4 | + | 0.465 | − | 0.025 | 8 mg/kg |
| P17 | week 8 | + | 0.409 | − | 0.026 | 8 mg/kg |
| P18 | week 4 | + | 1.218 | − | 0.026 | 4 mg/kg |
| P18 | week 4 | + | 1.041 | − | 0.028 | 4 mg/kg |
| P5 | week 28 | + | 0.219 | + | 0.060 | 8 mg/kg |
| P6 | week 12 | + | 3.689 | + | 3.721 | 4 mg/kg |
| P6 | week 24 | + | 3.506 | + | 3.722 | 4 mg/kg |
| P6 | week 8 | + | 0.387 | + | 0.688 | 4 mg/kg |
| P22 | week24 | + | 0.423 | − | 0.020 | 4 mg/kg | study related CP: 0.215 (conventional ELISA); 0.058 (interference-suppressed ELISA); +: positive ELISA result; −: negative ELISA result The signal pattern with both assays is not similar: whereas 25 patients were determined to be positive using the conventional ELISA only 10 patients were determined to be positive using the interference-suppressed ELISA as reported herein.

Example 7

Influence of Kind of Derivatization of Capture and Tracer Reagents

Mono- vs. Multi-Labeling

Measures to increase drug tolerance consisting in increasing the concentration of biotinylated and digoxigenylated TCZ (e.g. to 1.5 µg/mL); this could cause higher background by sticky digoxigenin; To beware of worse drug tolerance due to higher cut-points, a mono biotinylation and mono digoxigenylation give lower background signals by presence of higher capture and tracer concentration.

A sandwich ELISA was used for both screening and confirmation of anti-drug antibodies (ADAs) against tocilizumab (TCZ) (see Stubenrauch, K., et al., Clin. Ther. 32 (2010) 1597-1609). The principle of the method is the capture of ADAs in complex with TCZ-Dig(mono) and TCZ-Bi(mono), the latter one leading to immobilization onto a streptavidin-coated plate. The TCZ-Bi/ADA/TCZ-Dig complex (pre-incubation overnight) bound to the SA-MTP was detected by an anti-Dig-HRP enzyme conjugated antibody. The principle of the drug-tolerant anti-drug antibody assay is shown in FIG. 1. Inclusion of oligomeric IgG as ADA assay additive leads to an interference-suppressed anti-drug antibody assay as shown in FIG. 2. The horseradish peroxidase (HRP) of the polyclonal antibody catalyzes a color reaction of the substrate ABTS. The color intensity is proportional to the concentration of the analyte.

The screening assay was performed at room temperature. Reagents and serum samples were diluted with Universal buffer (cat no. 4742672), all washing steps were performed with the washing buffer (PBS, 0.05% polysorbate 20 (Tween® 20) (cat. no. 11332465-001)) three times with 300 µL per well. Incubations were performed under shaking on a microtiter plate shaker (MTP shaker) at 500 rpm. Test samples, QC and CS samples were incubated overnight (16 hours) with the capture antibody TCZ-Bi and the detection antibody TCZ-Dig. Each well of the pre-incubation microtiter plate (MTP) was loaded with 225 µL of the capture/detection solution containing 1.667 µg/mL TCZ-Bi(mono) and 1.667 µg/mL TCZ-Dig (mono) with oligomeric human IgG ADA assay additive (AAA) and thereafter 25 µL of the respective samples were added. The resulting concentrations of TCZ-Bi(mono) and TCZ-Dig(mono) were 1.5 µg/mL each and the oligomeric human IgG had a concentration of 50 µg/mL. The loaded MTP was covered to prevent evaporation and incubated overnight. Duplicates of 100 µL of each well of the pre-incubation plate were transferred to the wells of a streptavidin-coated microtiter plate (SA-MTP) which was covered and incubated for 1 h.

After washing, the polyclonal anti-Dig Fab-HRP conjugate with a concentration of 25 mU/mL was added in a volume of 100 µL to each well and incubated for 1 h. After washing, the ABTS ready-to-use solution was added in 100 µL aliquots to each well and incubated for about 10 to 15 min. while shaking. The signal of the color-generating reaction was measured by an ELISA reader at 405 nm wavelength (reference wavelength: 490 nm). Absorbance values of each serum sample were determined in triplicates. The highest standard should reach an optical density (OD) between 1.8 and 2.2 arbitrary units (AU). The obtained OD data was used for generating the standard calibration curve by non-linear 4-paramter fit "Wiemer Rodbard" for calculating the sample concentration. A sample was confirmed as positive to ADAs if the recovery of the concentration was less than the specificity cut-point.

Figure 5:
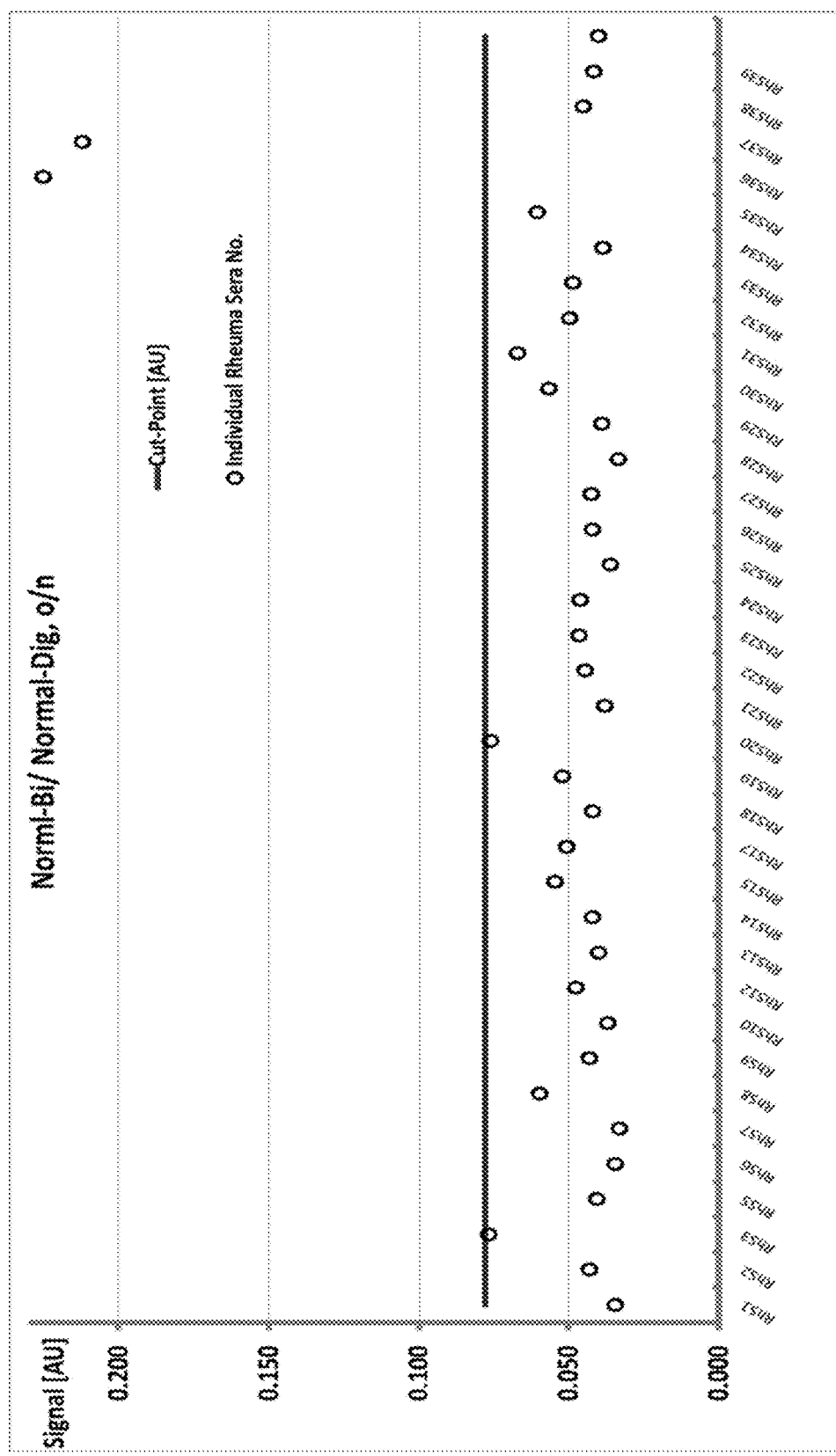
FIG. 5 Cut point determination with the interference-suppressed anti-drug antibody ELISA.
Figure 6:
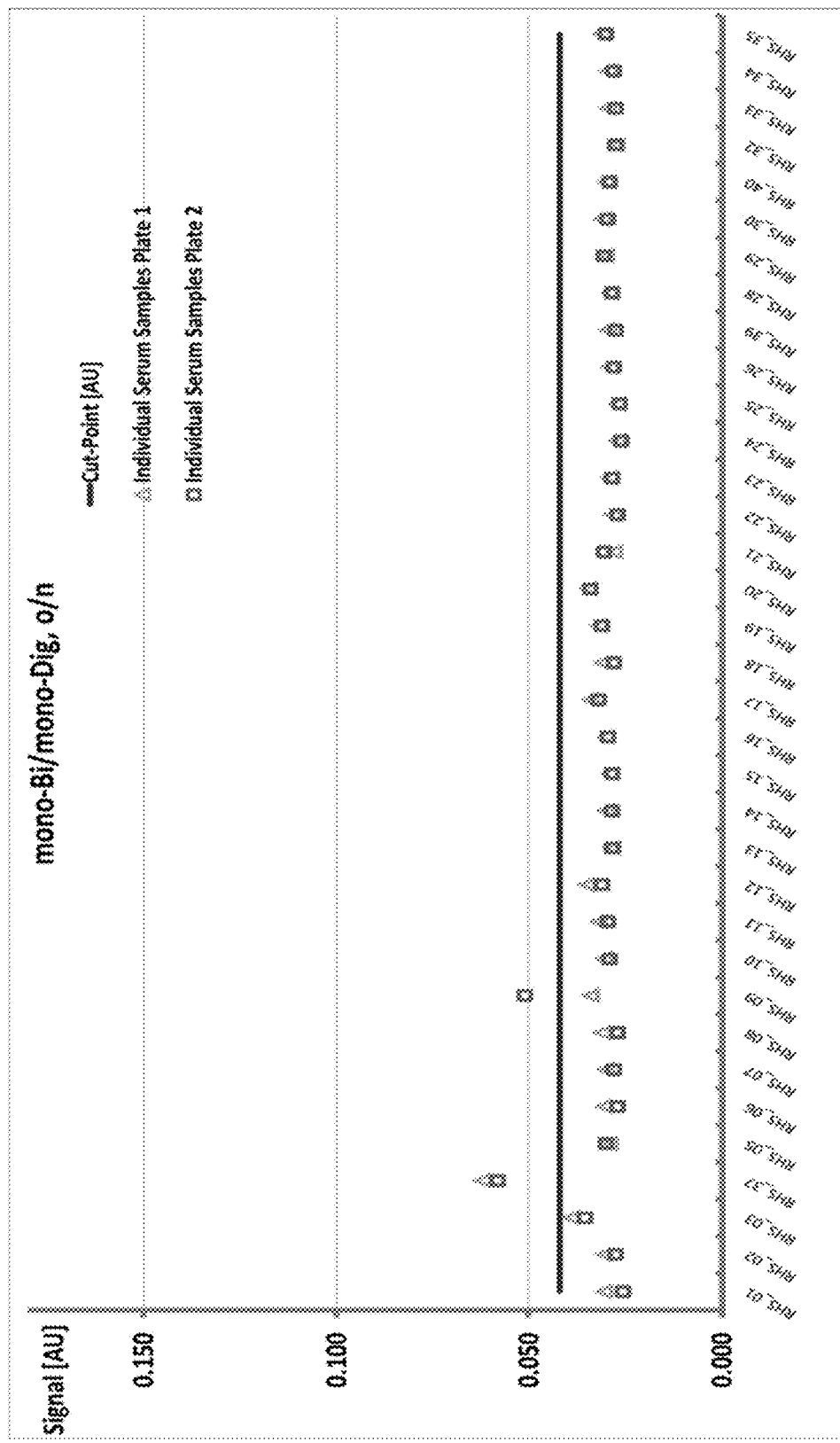
FIG. 6 Cut point determination with the interference-suppressed anti-drug antibody ELISA with TCZ-Bi(mono) and TCZ-Dig(mono).

To determine a cut point 35 native sera of patients with RD (rheumatic disease) were measured in both assays. As shown in FIGS. 5 and 6 the variances between the signals of the sera in the interference-suppressed anti-drug antibody ELISA compared to the interference-suppressed anti-drug antibody ELISA with TCZ-Bi(mono) and TCZ-Dig(mono) are high.

Figure 7:
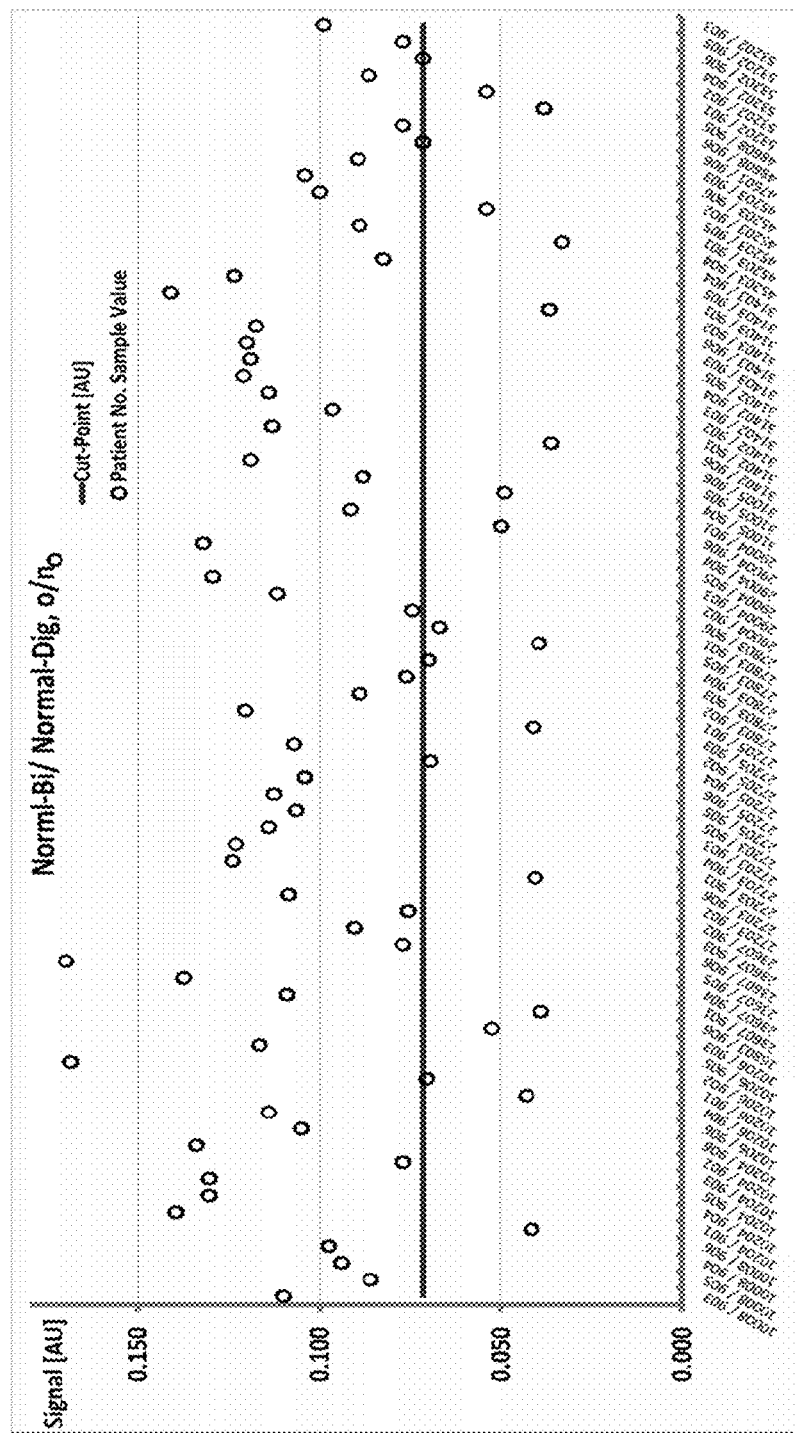
FIG. 7 Signal variations using conventional ELISA in 77 different serum samples from TCZ-treated RA patients.
Figure 8:
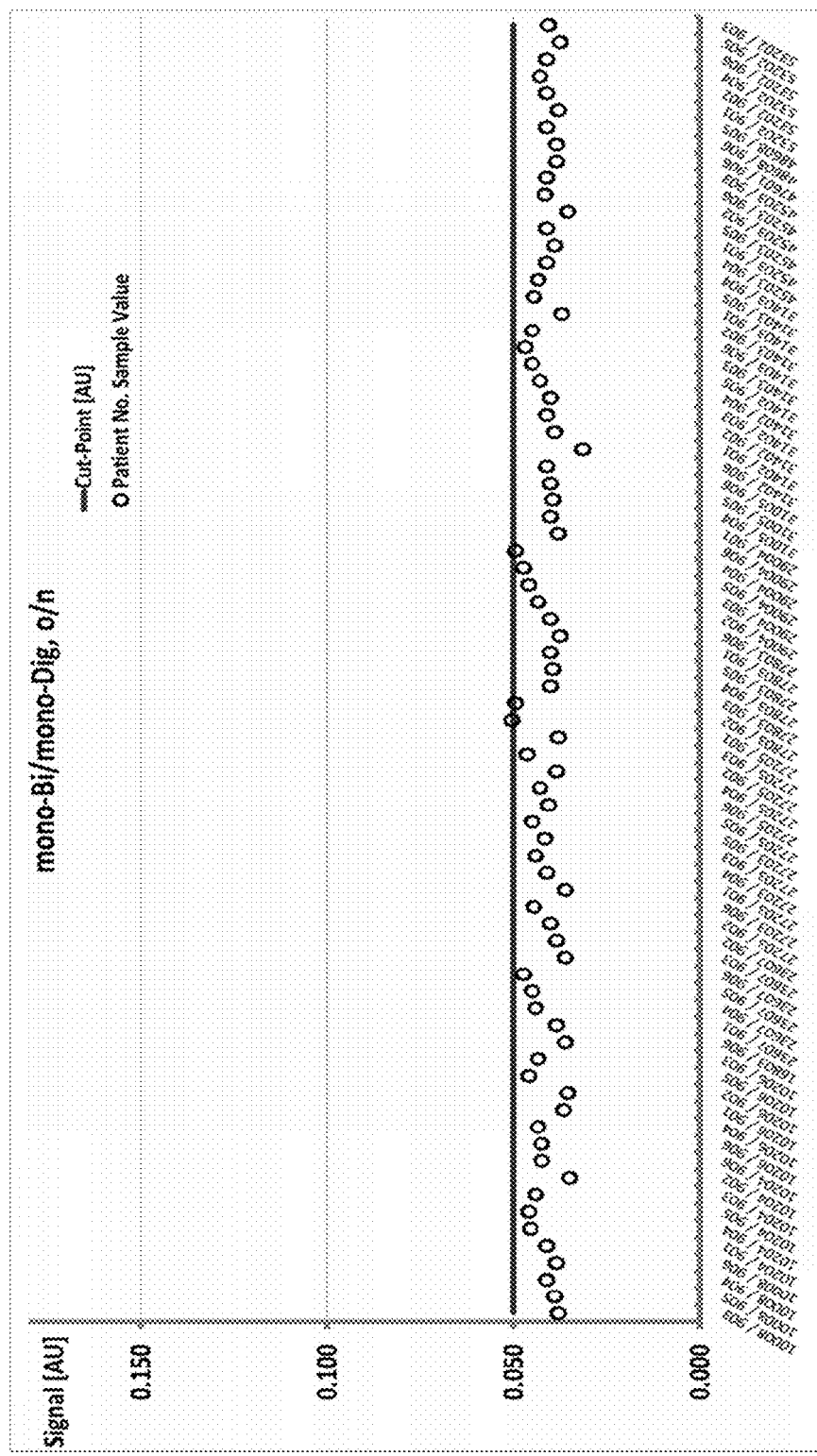
FIG. 8 Signal variations using the interference suppressed ELISA as reported herein in 77 different serum samples from TCZ-treated RA patients.

For further assessment 77 different serum samples from TCZ-treated RA patients were analyzed with both variants of interference-suppressed ADA-assay. Because all samples were taken before TCZ treatment (baseline), ADA against TCZ should be absent. Signals higher than cut point may indicated inference (false positives) not related with ADA against the treatment drug (TCZ), The assay with multi-labeled TCZ (FIG. 7) showed more signal variation than the assay with mono labeled TCZ (FIG. 8). As can be seen this variation is not a systemic setup of the system, which would simply be a shift on the Y-axis, but it is an increase in the bandwidth of obtained signals. Using these assay-specific cut points nearly all samples in the interference-suppressed drug-tolerant ADA assay (mono) are below cut point. Mostly all samples measured in the multi assay are above the cut point.

What is claimed is:

1. An interference-suppressed immunoassay for the detection of anti-drug antibodies against a drug antibody for the treatment of rheumatoid arthritis, juvenile arthritis, or osteoarthritis, said method comprising:
    (a) incubating a sample from a rheumatoid arthritis, juvenile arthritis, or osteoarthritis patient treated with said drug antibody simultaneously with a mixture comprising 0.5 µg/ml to 10 µg/ml of a 1:1 conjugate of said drug antibody to a first member of a binding pair via a single lysine residue as a capture drug antibody and 0.5 µg/ml to 10 µg/ml of a 1:1 conjugate of said drug antibody to a detectable label via a single lysine residue as a tracer drug antibody for 0.5 to 24 hours to generate a capture drug antibody/anti-drug antibody/tracer drug antibody complex, wherein the sample comprises 1% to 20% serum and is supplemented with oligomeric human IgG prior to the incubation to a final concentration of 10 µg/ml to 1000 µg/ml,
    (b) immobilizing the capture drug antibody/anti-drug antibody/tracer drug antibody complex formed in step (a) on a solid phase by covalently or non-covalently conjugating said first member of a binding pair to a second member of a binding pair on the solid phase,
    (c) incubating the immobilized complex with an antibody against the detectable label of the tracer drug antibody, conjugated to a second detectable label, and
    (d) detecting the anti-drug antibodies against said drug antibody via a signal of the detectable label of the antibody of step (c), and
    wherein the drug antibody is an anti-inflammatory antibody.
2. The method of claim 1, wherein the patient is a rheumatoid arthritis patient.
3. The method of claim 1, wherein the first member of a binding pair in said capture antibody is biotin, and the detectable label in said tracer antibody is digoxygenin.
4. The method of claim 3, wherein in step (b) the second member of a binding pair is streptavidin.
5. The method of claim 1 or 2, wherein the sample comprises anti-drug antibodies and rheumatoid factors.
6. The method of any one of claims 1 to 4, wherein the drug antibody is an anti-IL6R antibody.
7. The method of claim 6, wherein the anti-IL6R antibody is tocilizumab.

* * * * *

UNITED STATES PATENT AND TRADEMARK OFFICE
CERTIFICATE OF CORRECTION

PATENT NO. : 10,168,326 B2  
APPLICATION NO. : 15/078140  
DATED : January 1, 2019  
INVENTOR(S) : Kay-Gunner Stubenrauch and Rudolf Vogel Page 1 of 1

It is certified that error appears in the above-identified patent and that said Letters Patent is hereby corrected as shown below:

On the Title Page

Item (73) Assignee: reading "F. HOFFMANN-LA ROCHE INC." should read as
-- HOFFMANN-LA ROCHE INC. --

Signed and Sealed this
Seventh Day of January, 2020

Andrei Iancu
*Director of the United States Patent and Trademark Office*